US010105329B2

(12) United States Patent
Garrett et al.

(10) Patent No.: US 10,105,329 B2
(45) Date of Patent: *Oct. 23, 2018

(54) MODULATION OF REGULATORY T CELLS VIA G-COUPLED PROTEIN RECEPTOR 43

(71) Applicant: President and Fellows of Harvard College, Cambridge, MA (US)

(72) Inventors: Wendy S. Garrett, Brookline, MA (US); Patrick M. Smith, Foxborough, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/630,766

(22) Filed: Jun. 22, 2017

(65) Prior Publication Data

US 2017/0340588 A1 Nov. 30, 2017

Related U.S. Application Data

(62) Division of application No. 14/777,476, filed as application No. PCT/US2014/030832 on Mar. 17, 2014, now Pat. No. 9,693,977.

(60) Provisional application No. 61/800,299, filed on Mar. 15, 2013.

(51) Int. Cl.
*A61K 31/19* (2006.01)

(52) U.S. Cl.
CPC .................................... *A61K 31/19* (2013.01)

(58) Field of Classification Search
CPC ...................................................... A61K 31/19
See application file for complete search history.

(56) References Cited

U.S. PATENT DOCUMENTS

2016/0038447 A1 2/2016 Garrett et al.

FOREIGN PATENT DOCUMENTS

| JP | 2010-051307 | 3/2010 |
| WO | WO 2011/152566 | 12/2011 |
| WO | WO 2014/145970 | 9/2014 |

OTHER PUBLICATIONS

Garrett, Abstract, "Disease Initiation and the Role of Dcs in the Truc Model of Ulcerative Colitis," National Institutes of Health Grant No. 1K08AI078942-01A1 (Funding Start Date Mar. 1, 2009).
Garrett, Abstract, "Gut Microbiota and Inflammatory Monocytes in Colorectal Cancer," National Institutes of Health Grant No. 1R01CA154426-01 (Funding Start Date Mar. 18, 2011).
Maslowski, et al., "Regulation of Inflammatory Responses by Gut Microbiota and Chemoattractant Receptor GPR43," *Nature*, 461(7268):1282-1286, (2009).
Mimura, et al., "Once Daily High Dose Probiotic Therapy (VSL#3) for Maintaining Remission in Recurrent or Refractory Pouchitis," *Gut*, 53:108-114, (2004).
Saouaf, et al., "Deacetylase Inhibition Increases Regulatory T Cell Function and Decreases Incidence and Severity of Collagen-induced Arthritis," *Experimental and Molecular Pathology*, 87(2):99-104, (2009).
Smith, Abstract, "Interactions Between T Regulatory Cells & Gut Microbiota in Health & Disease," National Institutes of Health Grant No. 1F32DK095506-01 (Funding Start Date Mar. 1, 2012).
Ulven, "Short-Chain Free Fatty Acid Receptors FFA21GPR43 and FFA3/GPR41 as New Potential Therapeutic Targets," *Frontiers in Endocrinology*, 3(111):1-92, (2012).
Vinolo, et al., "Regulation of Inflammation by Short Chain Fatty Acids," *Nutrients*, 3:858-876, (2011).
Wang, et al., "Using Histone Deacetylase Inhibitors to Enhance Foxp3+ Regulatory T-Cell Function and Induce Allograft Tolerance," *Immunology and Cell Biology*, 87:195-202, (2009).
Wong, et al., "Colonic Health: Fermentation and Short Chain Fatty Acids," *J. Clin. Gastroenterol.*, 40(3):235-243, (Mar. 2006).
Zhang, et al., "Valproic Acid Ameliorates Inflammation in Experimental Autoimmune Encephalomyelitis Rats," *Neuroscience*, 221:140-150, (2012).
International Search Report for International Application PCT/US2014/30832, dated Aug. 25, 2014.
Final Office Action for U.S. Appl. No. 14/777,476, dated Nov. 29, 2016.

*Primary Examiner* — Robert S Landsman
(74) *Attorney, Agent, or Firm* — Nixon Peabody LLP

(57) ABSTRACT

Disclosed herein are compositions and methods that are useful for inducing the development of regulatory T cells ($T_{reg}$). Such compositions and methods are useful for treating inflammatory conditions and in particular inflammatory conditions affecting the gastrointestinal tract of a subject. In certain embodiments, the present inventions generally relate to short chain fatty acids and the discovery that such short chain fatty acids may be used to treat and/or prevent inflammatory conditions by enhancing the size and immune function of a subject's endogenous $T_{reg}$ population.

8 Claims, 41 Drawing Sheets

Specification includes a Sequence Listing.

MODULATION OF REGULATORY T CELLS VIA G-COUPLED PROTEIN RECEPTOR 43

RELATED APPLICATIONS

This application is a divisional of U.S. application Ser. No. 14/777,476, filed Jan. 4, 2016, which is a national stage filing under 35 U.S.C. 371 of International Application No. PCT/US2014/030832, filed Mar. 17, 2014, which claims the benefit of U.S. Provisional Application No. 61/800,299, filed Mar. 15, 2013, the entire teachings of which are incorporated herein by reference.

GOVERNMENT SUPPORT

This invention was made with government support under grant numbers R01CA154426, F32DK095506 and K08AI078942 awarded by the National Institutes of Health. The government has certain rights in the invention.

BACKGROUND OF THE INVENTION

Humans are colonized from birth with trillions of bacteria, the majority of which reside within the intestinal tract and constitute the gut microbiota (Turnbaugh et al., *Nature* 449, 804-810 (2007)). Over the millennia the intestinal immune system has co-evolved with the gut microbiota to develop a number of highly regulated interactions required for the maintenance of intestinal health. Disruption of this homeostasis leads to intestinal inflammation and is generally regarded as a root cause of inflammatory bowel disease (Hooper, et al., *Science* 336, 1268-1273 (2012)).

Regulatory T cells ($T_{reg}$) are a subpopulation of T cells that are capable of modulating immune responses, and in particular modulating autoimmune responses. Those $T_{reg}$ expressing the transcription factor Foxp3 (i.e., Foxp3$^+$ $T_{reg}$) are particularly important for limiting intestinal inflammation (Izcue, et al. *Rev.* 212, 256-271 (2006); Josefowicz, et al. *Annu. Rev. Immunol.* 30, 531-564 (2012)). Colonic regulatory T cells ($cT_{reg}$) represent a subpopulation of $T_{reg}$ that are active in the gastrointestinal tract and are critical for regulating intestinal inflammation. Germ-free mice, which lack bacteria, have decreased numbers of $cT_{reg}$ and as a result are more susceptible to certain experimental colitis models, therefore suggesting that $cT_{reg}$ depend on signals derived from the microbiota for their proper development and function (Geuking et al., *Immunity* 34, 794-806 (2011); Atarashi et al., *Science* 331, 337-341 (2011); Maslowski et al., *Nature* 461, 1282-1286 (2009); Atarashi, et al., *Semin. Immunol.* 23, 146-153 (2011)).

To date, it remains unclear how gut microbiota induce $cT_{reg}$ responses, and the identification of compounds that promote adaptive immune maturation and influence intestinal $T_{reg}$ and $cT_{reg}$ remain critical to understanding how intestinal homeostasis is maintained and how it can be optimized to promote health. Additionally, novel therapies are needed for modulating autoimmune and inflammatory responses, and in particular autoimmune and immune responses affecting the gastrointestinal tract. Particularly needed are safe and effective therapies that are capable of inducing (e.g., enhancing) a subject's ability to mount an immune response. Also needed are safe and effective therapies that enhance the production and/or activation, or otherwise increase the quantity and/or function of, $T_{reg}$ in the gastrointestinal tract of a subject.

SUMMARY OF THE INVENTION

The present inventors have discovered and disclose herein the mechanisms by which gut microbiota induce colonic regulatory T cell ($cT_{reg}$) responses as well as compounds and agents that promote adaptive immune maturation and influence intestinal $T_{reg}$. Also disclosed herein are novel compositions and methods that are useful for treating or otherwise modulating (e.g., reducing or otherwise improving) autoimmune and inflammatory responses and in particular modulating autoimmune and inflammatory responses involving the gastrointestinal tract (e.g., treating colonic inflammation and inflammatory bowel diseases). The compositions and methods disclosed herein can be used to modulate (e.g., increase, expand or otherwise improve) the quantity and/or the activity of colonic regulatory T cells ($cT_{reg}$), and thereby treat or prevent diseases or conditions having an inflammatory or autoimmune component.

In certain embodiments the inventions disclosed herein relate to methods of increasing the quantity of $cT_{reg}$, wherein such methods comprise a step of contacting a regulatory T cell ($T_{reg}$) with an effective amount of a composition to thereby increase the quantity of $cT_{reg}$, and wherein the composition comprises one or more compounds capable of modulating (e.g., interacting with) a G-coupled protein receptor 43 (GPR43). In some embodiments, the compounds comprise short chain fatty acids (e.g., one or more of formic acid, acetic acid, propionic acid, butyric acid, isobutyric acid, valeric acid, isovaleric acid and pharmaceutically acceptable salts, esters and pro-drugs thereof). In some embodiments, the compounds are G-coupled protein receptor 43 (GPR43) agonists.

Also provided herein are methods of increasing the function or activity of $cT_{reg}$ (e.g., a Foxp3$^+$ $cT_{reg}$) in the gastrointestinal tract of a subject, wherein the method comprises a step of contacting the $cT_{reg}$ with a composition comprising one or more short chain fatty acids and thereby increasing $cT_{reg}$ function or activity. For example, such methods may be employed to suppress an autoimmune response in a subject (e.g., a human subject with graft versus host disease).

In certain embodiments the inventions disclosed herein relate to methods of increasing the suppressive capacity of $cT_{reg}$, wherein such methods comprise a step of contacting the $cT_{reg}$ (e.g., a Foxp3$^+$ and/or IL-10$^+$ $cT_{reg}$) with a composition comprising one or more short chain fatty acids and thereby increasing the suppressive capacity of the $cT_{reg}$.

The inventions disclosed herein also relate to methods of increasing the quantity or concentration of $cT_{reg}$, wherein such methods comprise a step of contacting a $T_{reg}$ (e.g., Foxp3$^+$/IL-10$^+$ $T_{reg}$) with a composition comprising one or more short chain fatty acids (e.g., propionic acid and pharmaceutically acceptable salts, esters and pro-drugs thereof) and thereby increasing the quantity of the $cT_{reg}$.

In still other embodiments, the inventions disclosed herein relate to methods of modulating a $cT_{reg}$ immune response in the gastrointestinal tract of a subject, wherein such methods comprise administering an effective amount of a composition to the subject and thereby modulating $cT_{reg}$ immune response, and wherein the composition comprises one or more short chain fatty acids (e.g., propionate). In some embodiments modulating $cT_{reg}$ immune response comprises one or more of increasing the quantity of $cT_{reg}$ and increasing the function or activity (e.g., the suppressive activity) of $cT_{reg}$.

In certain embodiments, the inventions disclosed herein relate to methods of treating or preventing colonic inflammation in a subject, wherein such methods comprise a step of administering an effective amount of a composition to the subject and thereby treating or preventing colonic inflammation, wherein the composition comprises one or more short chain fatty acids, and wherein the composition increases immune function of $cT_{reg}$ in the gastrointestinal tract of the subject.

Also disclosed are methods of reducing the incidence of relapse of inflammatory bowel diseases (IBD) in a subject, wherein such methods comprise administering an effective amount of a composition to the subject and thereby reducing the incidence of relapse of IBD, wherein the composition comprises one or more short chain fatty acids, and wherein the composition modulates the immune response of the subject's $cT_{reg}$ (e.g., a Foxp3$^+$/IL-10$^+$ $cT_{reg}$). For example, the administration of such compositions (e.g., compositions comprising one or more short chain fatty acids) may cause an increase in the quantity or enhance the function of $cT_{reg}$, thereby providing an improved therapeutic benefit and reducing the incidence of relapse of IBD.

In certain embodiments, also disclosed herein are methods of increasing the expression of Foxp3 and IL-10 in Foxp3$^+$ and IL-10$^+$ $T_{reg}$, wherein such methods comprise a step of contacting the $T_{reg}$ with a composition comprising one or more short chain fatty acids and thereby increasing expression of Foxp3 and IL-10.

In some embodiments, the $T_{reg}$ express Ffar2 or otherwise comprise a GPR43. In certain embodiments, the compositions comprise one or more compounds or agents (e.g., short chain fatty acids) that modulate, interact with (e.g., bind to) or otherwise target the GPR43. The modulation or interaction of such compounds or agents (e.g., short chain fatty acids) with the GPR43 inhibits histone deacetylase (HDAC). For example, in certain embodiments, the short chain fatty acids disclosed herein (e.g., propionate) may modulate or interact (e.g., bind to) one or more GPR43 and thereby inhibit HDAC.

In certain embodiments, the modulation of the $cT_{reg}$ (e.g., modulation of the $cT_{reg}$ immune response in the gastrointestinal tract of a mammalian subject) is mediated through HDAC inhibition. In some embodiments, the increase in the suppressive capacity of $cT_{reg}$ is mediated through HDAC inhibition. In other embodiments, the observed increase in the quantity of $cT_{reg}$ is mediated through HDAC inhibition by the one or more short chain fatty acids.

In certain embodiments disclosed herein, the $T_{reg}$ or $cT_{reg}$ is Foxp3$^+$. In certain embodiments disclosed herein, the $T_{reg}$ or $cT_{reg}$ is IL-10$^+$. In yet other embodiments, the $T_{reg}$ or $cT_{reg}$ is capable of expressing and/or producing IL-10.

The compounds and methods disclosed herein are particularly suitable for treating inflammatory conditions (e.g., inflammatory bowel disease) and autoimmune conditions involving the gastrointestinal tract. In some embodiments, the inventions relate to methods of treating colonic inflammation, for example, treating a subject (e.g., a human subject) suffering from or otherwise affected by colonic inflammation that is secondary to an autoimmune disease (e.g., graft versus host disease). In certain embodiments, the inventions relate to methods of treating inflammation, for example, treating a subject (e.g., a mammal) having inflammation that is secondary to inflammatory bowel disease (e.g., Crohn's disease).

Also disclosed herein are compositions (e.g., pharmaceutical compositions) that comprise one or more agents or compounds that are capable of modulating or otherwise interacting with GPR43. In certain embodiments, the compositions disclosed herein generally comprise one or more short chain fatty acids. For example, the one or more short chain fatty acids may be selected from the group consisting of formic acid, acetic acid, propionic acid, butyric acid, isobutyric acid, valeric acid, isovaleric acid and pharmaceutically acceptable salts, esters or pro-drugs thereof. In certain embodiments, the short chain fatty acids comprise a mixture of one or more of formic acid, acetic acid, propionic acid, butyric acid, isobutyric acid, valeric acid, isovaleric acid and pharmaceutically acceptable salts, esters or pro-drugs thereof. In certain embodiments, such short chain fatty acids increase the quantity of $cT_{reg}$ (e.g., increase the concentration of $cT_{reg}$ in the colon of a human subject).

Also contemplated are methods of contacting $cT_{reg}$ ex vivo using the compositions disclosed herein (e.g., compositions comprising one or more short chain fatty acids). In such embodiments such $cT_{reg}$ may be contacted (e.g., contacted with one or more short chain fatty acids to increase their quantity or function) and subsequently are administered to a subject (e.g., to treat an inflammatory condition).

The invention also relates to methods of increasing expression of Foxp3 and IL-10 in Foxp3$^+$ and IL-10$^+$ regulatory T cells ($T_{reg}$), wherein the method comprises contacting the $T_{reg}$ with a composition comprising one or more short chain fatty acids (e.g., propionate) and thereby increasing expression of Foxp3 and IL-10. In some embodiments, the $T_{reg}$ are $cT_{reg}$. In other embodiments, the $T_{reg}$ express Ffar2 or a GPR43. In yet other embodiments, the interaction of the one or more short chain fatty acids with the GPR43 inhibits HDAC.

In certain embodiments, the methods and compositions disclosed herein increase the concentration of a GPR43 agonist in a subject (e.g., by increasing the concentration of short chain fatty acids within the colon of a subject). For example, in certain embodiments, the administration of short chain fatty acids (e.g., propionic acid, acetic acid and/or butyric acid) to a subject may result in such short chain fatty acid concentration of at least 5 µmol/g, 10 µmol/g, 15 µmol/g, 20 µmol/g, 25 µmol/g, 30 µmol/g, 35 µmol/g, 40 µmol/g, 45 µmol/g, 50 µmol/g, 55 µmol/g, 60 µmol/g, 65 µmol/g, 70 µmol/g, 75 µmol/g, 80 µmol/g, 85 µmol/g, 90 µmol/g, 95 µmol/g, 100 µmol/g, 200 µmol/g, 250 µmol/g, 500 µmol/g or more in the luminal contents of the subject. In certain embodiments, the concentration of propionate in the tissues of the colon is at least 0.1 mM. In certain embodiments, such concentrations of short chain fatty acids (e.g., propionic acid, acetic acid and/or butyric acid) are achieved by administering an effective amount (e.g., at least about 0.1 mM, 0.5 mM, 1 mM, 2.5 mM, 5 mM, 10 mM, 50 mM, 75 mM, 100 mM, 150 mM, 200 mM, 250 mM, 300 mM, 400 mM, 500 mM, 600 mM, 700 mM, 800 mM, 900 mM, 1000 mM, or more) of the short chain fatty acids on at least a daily basis (e.g., at least once, twice, three times, four times, five times, six times daily). In certain embodiments, an effective amount of GPR43 agonist (e.g., short chain fatty acids) that is administered to the subject is not achievable through dietary intake or dietary supplementation.

The above discussed and many other features and attendant advantages of the present invention will become better understood by reference to the following detailed description of the invention when taken in conjunction with the accompanying examples.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A depicts cecal SCFA levels that were measured from GF and specific pathogen-free (SPF) BALB/c WT mice by HPLC. Data represent the means and sum of 3 experiments with cecal contents from 3-5 age and sex-matched mice per group. FIG. 1B illustrates colonic lamina propria (LP) lymphocytes that were isolated and stained for CD4 and Foxp3. Upper panel: Representative flowgrams and % $CD4^+Foxp3^+$ within the $CD45^+CD3^+$ population from SPF, GF, and GF mice treated with propionic acid (P), acetic acid (A), butyric acid (B), or the SCFA mix (MIX) in the drinking water. Lower panel: Numbers of $Foxp3^+$ $T_{reg}$ for the upper panel. FIG. 1C illustrates that SCFA expand $Foxp3^+Helios^+$ $T_{reg}$ in the colon of GF free mice. Colonic LP lymphocytes were isolated from SPF, GF, and GF mice treated with P, A, B or the SCFA mix in the drinking water for three weeks and stained for CD45, CD4, Helios, and Foxp3. Upper panel: Representative flowgrams and percentage of $Foxp3^+CD4^+$ population with Helios staining. Lower panel: Numbers of $Helios^+Foxp3^+$ $T_{reg}$ for the upper panel. FIG. 1D illustrates colonic $T_{reg}$ ($CT_{reg}$) that were isolated from GF mice and purified by FACS staining for CD4, CD127, and CD25, cultured for 24 hours in the presence or absence of 0.1 mM propionate, and examined for expression of Foxp3, TGFβ and IL-10 mRNA by qPCR. FIG. 1E illustrates $cT_{reg}$ that were isolated from GF mice and purified as in FIG. 1D, cultured for 24 hours in the presence or absence of 0.1 mM propionate and examined for expression of Foxp3, TGFβ, and IL-10 by RTqPCR and IL-10 protein production by ELISA. FIG. 1F illustrates mice that were treated orally with vancomycin for 2 weeks and then also given P, A, B, or the SCFA mix. After 4 weeks, colonic LP lymphocytes were isolated and stained for CD4 and Foxp3. The percentage of $CD4^+Foxp3^+$ within the $CD45^+CD3^+$ population from SPF mice or vancomyin-treated SPF mice exposed to water alone (−), P, A, B, or the SCFA mix are shown. For FIG. 1B, symbols represent data from individual mice. Horizontal lines show the mean and error bars the SD. For FIGS. 1D and 1E, each symbol or bar represents pooled $cT_{reg}$ from 3-5 mice. All data shown are representative of at least 3 independent experiments. A Kruskal-Wallis test with a Dunn's post hoc test was performed in FIGS. 1B and 1F, *** $P<0.001$ and * $P<0.05$. A Mann-Whitney U test was performed in FIGS. 1D and 1E.

FIG. 4A depicts representative flowgrams of $CD45^+CD3^+CD4^+IFN\gamma^+$ populations. FIG. 4B in the upper right panel: Percentage of, and Lower right panel: Number of, $CD4^+IFN\gamma^+$ cells within the $CD45^+CD3^+$ population. FIG. 4C depicts representative flowgrams of $CD45^+CD3^+CD4^+IL-17^+$ populations. FIG. 4D in the Upper right panel: Percentage of, and Lower right panel: Number of, $CD4^+IL-17^+$ cells within the $CD45^+CD3^+$ population. Each symbol represents data from an individual mouse and data reflect 3 independent experiments. P-values are not shown as differences with SCFA treatment were not statistically significant. Horizontal lines show the mean and error bars the SD.

FIG. 5A illustrates the results of SPF $Foxp3^{YFP-Cre}$ mice that were treated with water alone (−) or propionic acid (P), acetic acid (A) or butyric acid (B), or the SCFA mix. Colonic lamina propria (LP) lymphocytes were isolated and stained for CD4 and IL-10. Upper panel: Representative dot plots and percentage of $CD4^+$ $Foxp3-YFP^+$ within the $CD45^+CD3^+$ population. Lower panel: Representative dot plots and percentage of the CD4+Foxp3+IL-10+population. FIG. 5B corresponds to the cell numbers for the data in FIG. 5A upper panel. FIG. 5C corresponds to the cell numbers for the data in FIG. 5A lower panel. Symbols in FIGS. 5B and 5C represent data from individual mice and represent 4 independent experiments. FIG. 5D illustrates that SCFA increase colonic $T_{reg}$ suppressive capacity. Colonic LP $T_{reg}$ and splenic effector T cells were isolated by FACS sorting. Splenic effector T cells were first labeled with CellTrace cell violet dye (5 μM) and cultured alone or co-cultured with $cT_{reg}$. Cultures were either unstimulated or stimulated with 1 μg/ml plate bound anti-CD3, 1 μg/ml soluble CD28 and P or pH and sodium matched media for 96 hrs. Flowgrams depicted are representative of three independent experiments. Significance is shown in FIG. 5E. Horizontal lines represent the mean and error bars the SD. FIG. 5E depicts the suppression of $cT_{reg}$ that were co-cultured with splenic effector T cells (Teff) and P, A, B, or media (sodium and pH matched) for 96 hours. Percent suppression (y-axis), Treg: Teff ratios (x-axis). Symbols represent mean values and error bars SD for four independent experiments. * $P<0.01$. FIG. 5F illustrates that in vitro treatment of colonic $T_{reg}$ with propionate increases Foxp3 and IL-10 expression, as well as IL-10 protein production. Colonic LP $T_{reg}$ were isolated from SPF $Foxp3^{YFP-Cre}$ mice, cultured for 24 hours in the presence or absence of 0.1 mM propionate, and examined for in vitro expression of Foxp3, and IL-10 by RTqPCR or secretion of IL-10 by ELISA. Upper left panel: expression of Foxp3. Upper middle panel: expression of TGFβ. Lower middle panel: TGFβ protein production. Upper right panel: expression of IL-10. Lower right panel: IL-10 protein production. Each symbol represents pooled colonic $T_{reg}$ from 3-4 mice and reflects data from at least 4 independent experiments. Mann-Whitney U test was performed to determine statistical significance. Horizontal lines represent the mean and error bars the SD.

FIG. 15A illustrates T$_{reg}$ that were isolated from the colon, small intestine, spleen and mesenteric lymph node (MLN) of specific pathogen-free (SPF) and germ-free (GF) BALB/c mice, purified as described in FIG. 1D and Ffar2 expression examined by qPCR. Each symbol represents data from 3-5 individual mice, horizontal lines show the mean and error bars the SD. Data reflect 3-7 independent experiments. FIG. 15B shows results of lymphocytes that were isolated from the colon, small intestine, spleen, and MLN of SPF Ffar2$^{-/-}$ and littermate Ffar2$^{+/+}$ mice. Cells were stained for CD4, Foxp3, and Ffar2. Left panel depicts a representative flow cytometry histogram comparing colonic Ffar2 expression in Ffar2$^{-/-}$ vs littermate Ffar2$^{+/+}$ mice. Right panel shows the mean fluorescent intensity (MFI) for Ffar2 for T$_{reg}$ from the indicated sites. Bars show the mean, error bars SD, and data reflect 4 independent experiments. FIG. 15C illustrates that Ffar2 receptor (GPR43) is highly expressed in colonic T$_{reg}$ and myeloid cells. Colonic lamina propria (LP) lymphocytes were isolated from SPF Ffar2$^{+/+}$ and Ffar2$^{-/-}$ mice, stained for CD45, CD4, Foxp3 and CD11b and the MFI was determined by flow cytometry. The MFI was calculated by averaging the geometric means for Ffar2 expression of individual mice. The bar graph shown is the average of 5 individual mice per group and is representative of 3 independent experiments. Horizontal lines represent the mean and error bars the SD. FIG. 15D depicts results of colonic LP lymphocytes that were isolated from Ffar2$^{-/-}$ and littermate Ffar2$^{+/+}$ mice exposed to propionate (P) or water alone and stained for CD4 and Foxp3. Left panel: Representative dot plots with percentage of CD4$^+$Foxp3$^+$ within the CD45$^+$ CD3$^+$ population. Right panel: Foxp3$^+$ T$_{reg}$ number for the left panel. Each symbol represents data from individual mice, horizontal lines show the mean and error bars the SD. FIG. 15E illustrates that Ffar2 is required for propionate-mediated increase of Foxp3 and IL-10 levels in colonic T$_{reg}$ from SPF mice. Colonic LP T$_{reg}$ were isolated from Ffar2$^{-/-}$ and littermate Ffar2$^{+/+}$ mice, purified as described in FIG. 1D, cultured in the presence of 0.1 mM propionate for 24 hours and examined for expression of Foxp3 and IL-10 by RTqFCR and secretion of IL-10 by ELISA. Each symbol represents pooled data from 3-5 mice and data are representative of 2 independent experiments. Student's t-test was performed to determine significance. Horizontal lines represent the mean and error bars the SD. FIG. 15F shows that Ffar2 is required for the propionate-mediated restoration of colonic T$_{reg}$ levels in SPF antibiotic treated mice. Ffar2$^{-/-}$ and littermate Ffar2$^{+/+}$ mice were treated orally with vancomycin for 4 weeks and also given propionate (P) in the drinking water starting in week 2. After 4 weeks, colon LP lymphocytes were isolated and stained for CD45, CD4 and Foxp3. The percentage and number of CD4$^+$Foxp3$^+$ cells within the CD45+ population are shown. Each symbol represents data from an individual mouse and data represent 2 independent experiments. Student's t-test was performed to determine significance. Horizontal lines represent the mean and error bars the SD. FIG. 15G shows the results of cT$_{reg}$ that were isolated from the LP of Ffar2$^{-/-}$ and littermate Ffar2$^{+/+}$ mice, purified as described in FIG. 1D, cultured in the presence of 0.1 mM propionate or media (pH and sodium matched) for 24 hours and examined for expression of HDAC 1, 2, 6, 7 and 9 by RTqFCR. Bars show the mean and error bars the SD of 3 independent experiments. FIG. 15H depicts results of Ffar2$^{-/-}$ and littermate Ffar2$^{+/+}$ cT$_{reg}$ that were co-cultured with splenic T$_{eff}$ cells in media with or without propionate for 96 hours. Percent suppression (y-axis) and T$_{reg}$:T$_{eff}$ ratios (x-axis). Symbols represent the mean of 3 independent experiments and error bars show the SD. FIG. 15I present the results of whole cell extracts that were generated from cT$_{reg}$ isolated from the LP of Ffar2$^{-/-}$ and littermate Ffar2$^{+/+}$ mice, purified as described in FIG. 1D, and cultured in the presence of 0.1 mM propionate or media (pH and sodium matched) for 24 hours. Samples were analyzed by Western blotting for histone acetylation by examining levels of acetylated histone (H3K9), total histone levels were used as a loading control. The Western blot shown is representative of two independent experiments with cT$_{reg}$ cell lysates pooled from 10-12 mice per group. A bar graph of densitometry ratios of acetylated Histone H3:total Histone H3 is shown. Bars represent the mean and error bars the SD. A Kruskal-Wallis test with a Dunn's post hoc test was performed for FIGS. 15A and 15H, * P<0.001. The Mann-Whitney U test was performed for FIGS. 15D and 15G. The student's t-test was performed for FIGS. 15B and 15I**.

FIG. 16A shows the histologic colitis score along the y-axis, the treatment groups and experimental conditions are shown along the x-axis. FIG. 16B illustrates representative H&E images for the experimental groups. Propionate and SCFA treated mice show reduced degrees of colonic crypt injury, inflammation, and hyperplasia compared to control mice. A 100 μm scale bar is shown in the lower left of each image. One-way ANOVA with Bonferroni post-hoc is shown in FIG. 16A. Horizontal lines represent the mean and error bars the SD.

FIG. 17A depicts the weekly percentage body weight change across the experimental groups from experimental day 0 through day 42. Symbols show the mean and error bars the SD. Data reflect three independent experiments. Colonic lamina propria (LP) lymphocytes were isolated and stained for CD4 and Foxp3 and percentage and number of CD4$^+$Foxp3$^+$ within the CD45$^+$CD3$^+$ population are shown in FIGS. 17B and 17C, respectively. Symbols represent data from individual mice, horizontal lines show the mean and error bars the SD. FIGS. 17D-F show the results of C57BL/6 Rag2$^{-/-}$ mice that were injected with CD4$^+$CD45RB$^{hi}$CD25$^{lo}$ naïve T cells alone or in combination with Ffar2$^{+/+}$ or Ffar2$^{-/-}$ T$_{reg}$. Following injection mice received propionate or pH and sodium-matched drinking water. In FIG. 17D, histologic colitis score is shown along the y-axis, and the treatment group and experimental conditions are shown along the x-axis. Colonic LP lymphocytes were isolated and percentage and number of CD4$^+$Foxp3$^+$ within the CD45$^+$CD3$^+$ population are shown in FIGS. 17E and 17F, respectively. Symbols represent data from individual mice. Horizontal lines show the mean and error bars the SD. FIGS. 17D-17F represent data from 2 independent experiments. The Kruskal-Wallis test with a Dunn's post hoc test was performed for FIGS. 17A-17F. ** P<0.01, * P<0.05.

DETAILED DESCRIPTION OF THE INVENTION

Figure 1A:
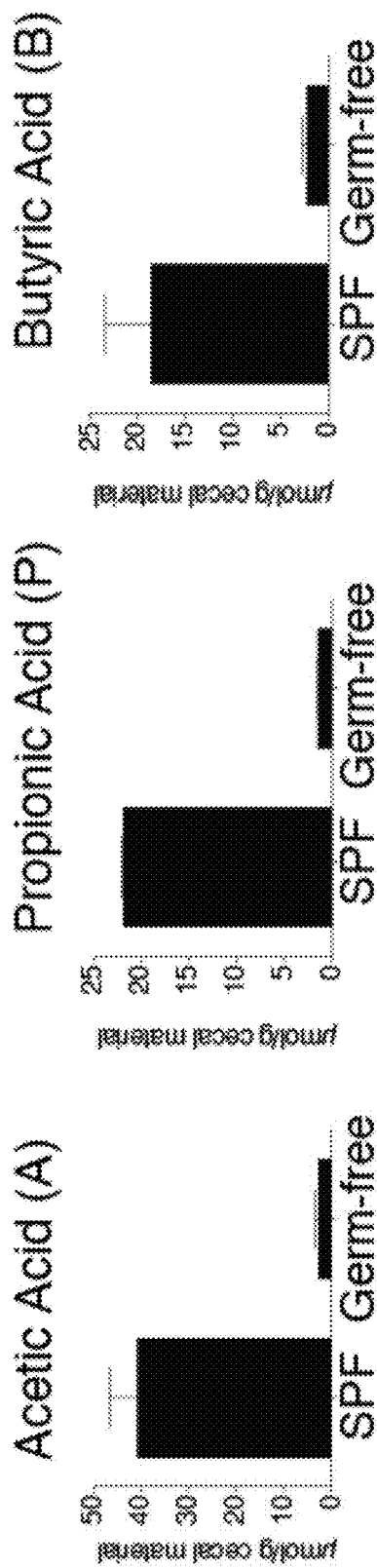
FIGS. 1A-1F illustrate that short chain fatty acids (SCFA) restore colonic $T_{reg}$ populations and function in germ-free (GF) and antibiotic treated mice.

The inventions described herein generally relate to the findings that short chain fatty acids (SCFA) play a critical role in the induction of regulatory T cells ($T_{reg}$), and in particular colonic regulatory T cells ($cT_{reg}$). $T_{reg}$ are a subpopulation of T cells that are capable of modulating immune responses and those $T_{reg}$ expressing the transcription factor Foxp3 (i.e., Foxp3$^+$ $T_{reg}$) are particularly important for limiting intestinal inflammation (Izcue, et al. *Rev.* 212, 256-271 (2006); Josefowicz, et al. *Annu. Rev. Immunol.* 30, 531-564 (2012)). $cT_{reg}$ are a subpopulation of $T_{reg}$ that are active in the gastrointestinal tract and are involved in maintaining colonic homeostasis and limiting inflammation of the gastrointestinal tract.

Disclosed herein are the mechanisms pursuant to which SCFA mediate $cT_{reg}$ responses, and thereby mitigate intestinal inflammatory responses (e.g., inflammatory responses related to inflammatory bowel diseases). Also disclosed are novel compositions and optimized methods of maintaining intestinal homeostasis and of treating or preventing colonic inflammation.

The methods and compositions disclosed herein are useful for the treatment of inflammatory conditions, and in particular colonic inflammation. As is used herein, the phrase "colonic inflammation" broadly refers to any inflammatory disease, disorder or pathological condition affecting the cells and tissues of the gastrointestinal tract. Exemplary involving colonic inflammatory conditions include inflammatory bowel disease, pouchitis, aging, irritable bowel syndrome, and cancer of the gastrointestinal tract, obesity and type II diabetes. In certain embodiments, the colonic inflammation is secondary to an immune disorder or an autoimmune disorder. For example, the compositions and methods disclosed herein may be employed to treat or otherwise reduce colonic inflammation which occurs as a result of, or is otherwise associated with graft versus host disease.

In certain embodiments, the methods and compositions disclosed herein may be employed to treat or prevent relapses of inflammatory bowel disease (IBD). For example, disclosed herein are methods of reducing the incidence of relapse of IBD in a subject, by administering an effective amount of a composition comprising one or more short chain fatty acids to a subject. As used herein, the phrases "inflammatory bowel disease" and "IBD" broadly refer to a set of chronic, idiopathic, immune-mediated disorders that result in the inflammation of the gastrointestinal tract, and such phrases collectively include each of ulcerative colitis, Crohn's disease, irritable bowel syndrome, cancers of the gastrointestinal tract and pouchitis.

The present inventions are generally based upon the findings that short chain fatty acids (SCFA) are capable of mediating the $T_{reg}$ immune response (e.g., the $cT_{reg}$ immune response) by increasing or otherwise stimulating $T_{reg}$ numbers and functional capacity and thereby modulating (e.g., increasing or otherwise enhancing) a subject's (e.g., a human subject's) immune response. Such findings therefore provide means of influencing the degree to which $T_{reg}$ participate in an inflammation- or immune-mediated condition (e.g., colonic inflammation and/or IBD) and provide means of restoring intestinal homeostasis to thereby treat colonic inflammation.

As used herein, the phrases "short chain fatty acids" and "SCFA" generally refer to fatty acids having less than about ten carbons in the carbon backbone and salts, esters and pro-drugs thereof. Exemplary SCFA include formic acid, acetic acid, propionic acid, butyric acid, isobutyric acid, valeric acid, isovaleric acid and pharmaceutically acceptable salts thereof. In certain embodiments, the short chain fatty acids comprise a mixture of one or more of formic acid, acetic acid, propionic acid, butyric acid, isobutyric acid, valeric acid, isovaleric acid and pharmaceutically acceptable salts, esters or pro-drugs thereof. In certain embodiments, the short chain fatty acids comprise a mixture of propionic acid, acetic acid and butyric acid.

The present inventions are also based on the findings that SCFA mediate the induction of $T_{reg}$, and in particular $cT_{reg}$, by way of the G-coupled protein receptor 43 (GPR43) and that GPR43 is necessary for SCFA-mediated $cT_{reg}$ induction. As discussed in greater detail below, GPR43 is encoded by the Ffar20 gene and is required for complete induction of $cT_{reg}$ by SCFA. It should be noted that while certain aspects of the present inventions contemplate the induction of $cT_{reg}$ using SCFA, such inventions are not limited to SCFA. Also disclosed are compositions and related methods of inducing (e.g., increasing the number and/or function) $cT_{reg}$ by contacting a $T_{reg}$ or a $cT_{reg}$ with one or more compounds capable of modulating (e.g., interacting with or binding to) a GPR43 receptor.

In certain embodiments, the compositions and methods disclosed herein cause an increase in the quantity of $cT_{reg}$. Similarly, in some embodiments, the compositions and methods disclosed herein augment (e.g., enhance, promote or increase) the native or natural function (e.g., the suppressive capacity) of $cT_{reg}$. By increasing the quantity and/or function of $cT_{reg}$, such $cT_{reg}$ are able to exert suppressive properties in the gastrointestinal tract to a greater degree. As used herein to describe $T_{reg}$, the phrase "suppressive capacity" generally refers to the functional ability of $T_{reg}$ to suppress inflammatory or immune-mediated responses. In certain embodiments, the suppressive capacity of $cT_{reg}$ is a function of the quantity of $cT_{reg}$ available to exert their effects in the gastrointestinal tract of a subject. In other embodiments, the suppressive capacity of $cT_{reg}$ relates to the functional ability of the $cT_{reg}$ in the gastrointestinal tract of a subject. The ability of the SCFA disclosed herein to augment, increase or otherwise enhance $T_{reg}$ function and quantity, represents a clinically significant advancement and can be applied to restore intestinal homeostasis and treat, prevent or otherwise ameliorate intestinal or colonic inflammation.

The present inventors have also discovered that the GPR43-mediated increases in the quantity and suppressive capacity of $cT_{reg}$ occurs through histone deacetylase (HDAC) inhibition. In certain embodiments, the SCFA disclosed herein (e.g., propionate) increase the quantity and suppressive capacity of $cT_{reg}$ by reducing $cT_{reg}$ expression of HDAC6 (Class IIB) and/or HDAC9 (Class IIA).

In certain embodiments, the $T_{reg}$ or $cT_{reg}$ that is contacted or the activity or quantity of which is otherwise modulated expresses Foxp3 or is Foxp3$^+$. In certain embodiments, such $T_{reg}$ or $cT_{reg}$ expressed IL-10 or is IL-10$^+$. In yet other embodiments, such $T_{reg}$ or $cT_{reg}$ is capable of expressing and/or producing IL-10.

In certain aspects, the methods of the present invention comprise the administration of an effective amount of one or more SCFA (e.g., acetic acid and pharmaceutically acceptable salts thereof) to a subject having colonic inflammation (e.g., an immune-mediated disease or ulcerative colitis). As used herein, the term "subject" means any mammal, including humans. In certain embodiments of the present invention the subject is an adult or an adolescent.

In certain embodiments, the inventions disclosed herein relate to methods of contacting $cT_{reg}$ ex vivo using the compositions disclosed herein (e.g., compositions comprising one or more short chain fatty acids). As the term is used herein, "contacting" generally refers to bringing two or more molecules or entities into close proximity with each other such that such molecules or entities can react or otherwise interact with each other. A step of contacting may be performed in vitro, ex vivo, in vivo. For example, in some embodiments a $cT_{reg}$ may be contacted with one or more short chain fatty acids (e.g., to increase the quantity or function of such $cT_{reg}$) and subsequently are administered to a subject (e.g., to treat an inflammatory condition).

As used herein, the phrase "effective amount" means an amount sufficient to achieve a meaningful benefit (e.g., improving or otherwise ameliorating colonic inflammation and/or maintaining intestinal homeostasis). An effective amount of the SCFA (e.g., butyric acid) in the compositions of the present invention may be generally determined based on the ability of such SCFA to stimulate or promote the quantity or function of $cT_{reg}$. Generally, the amount of SCFA administered to a subject will depend upon the characteristics of the subject and the severity of the subject's colonic inflammation. In certain embodiments, the compositions may be administered to a subject (e.g., administered orally) once daily, twice daily, three times daily, four times daily, five times daily, six times daily, seven times daily, eight times daily, or more.

The compositions of the present invention can be administered to a subject by any suitable routes of administration. Preferably, following the administration of such compositions a therapeutic concentration of the SCFA (e.g., acetate) is achieved and/or maintained in the tissues of the gastrointestinal tract (e.g., within the lumen of the gastrointestinal tract). For example, in certain embodiments, the compositions achieve and/or maintain a concentration of at least 5 mM, 10 mM, 25 mM, 40 mM, 50 mM, 60 mM, 75 mM, 100 mM, 125 mM, 150 mM, 175 mM, 200 mM, 250 mM, 300 mM, 400 mM, 500 mM or more within the lumen of the gastrointestinal tract. In certain embodiments, the composition is combined with suitable excipients and formulated for enteral or rectal administration. Alternatively, in certain embodiments, the compositions of the present invention may be prepared for parenteral administration. General techniques applicable to the formulation and administration of the compositions of the present invention may be found in "Remington's Pharmaceutical Sciences," Mack Publishing Co., Easton, Pa., latest edition.

The compositions of the present invention can also be administered or co-administered as part of a therapeutic regimen with other suitable therapeutic or prophylactic agents (e.g., administered concurrently or sequentially). For example, the compositions disclosed herein may be formulated or co-administered with one or more additional therapeutic agents (e.g., one or more non-steroidal anti-inflammatory drugs, corticosteroids, chemotherapeutics, immunosuppressants and antibiotics).

In embodiments where the compositions are administered to a subject orally, such compositions may be prepared or formulated as a dietary supplement or as a functional or medical food. In other embodiments, such compositions may be prepared or formulated, for example, as a pharmaceutical.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The entire contents of all of the references (including literature references, issued patents and published patent applications and websites) cited throughout this application are hereby expressly incorporated by reference.

EXAMPLES

Example 1

Humans and mice rely on bacteria to breakdown un-digestible materials ingested as part of their diets, such as fibers and other complex polysaccharides. The main end products of this bacterial fermentation are short chain fatty acids (SCFA). In the present study, concentrations of SCFA in specific pathogen-free (SPF) mice, gnotobiotic Altered Schaedler Flora (ASF)-colonized mice, and germ-free (GF) mice were evaluated and, as depicted in FIG. 1A, GF mice had reduced concentrations of the three most abundant luminal SCFA, acetic acid, propionic acid and butyric acid (see, Table 1 below). This substantial decrease of the three most abundant luminal SCFA in GF mice suggests that SCFA may contribute to some of the immune defects observed in GF mice and in particular the reduced number of $cT_{reg}$.

Figure 1B:
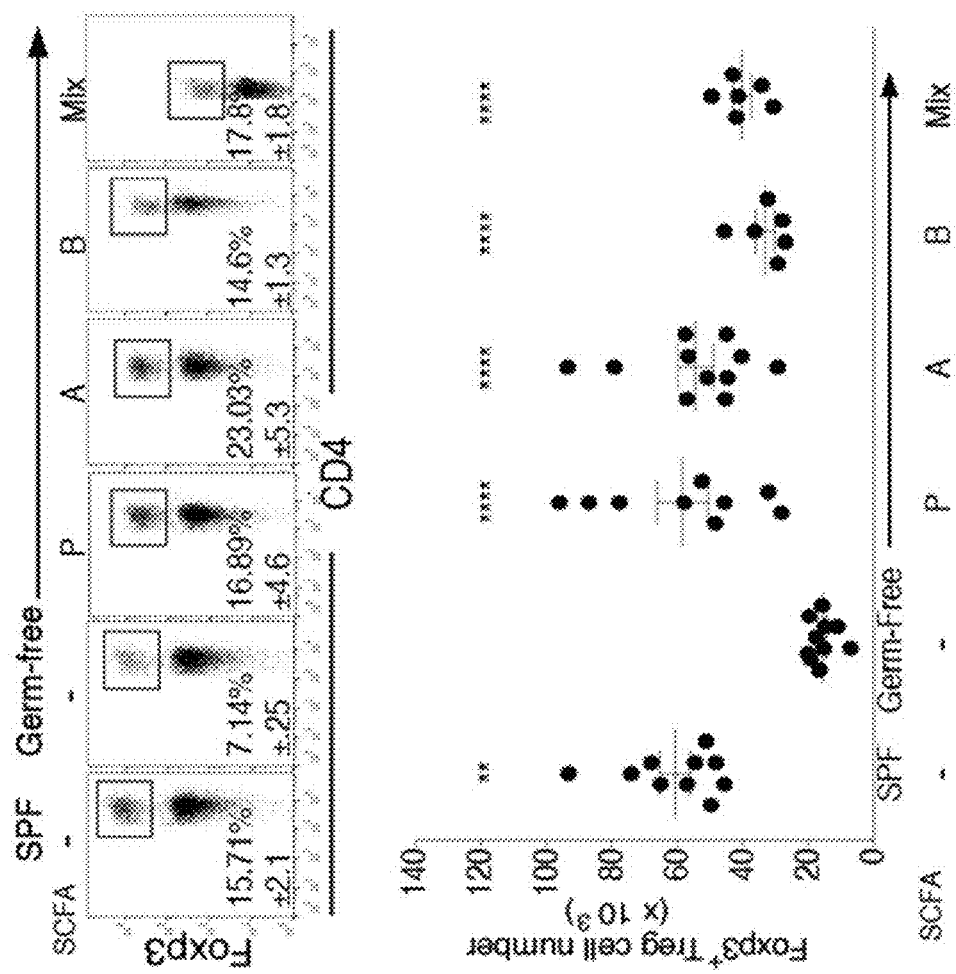
Figure 2A:
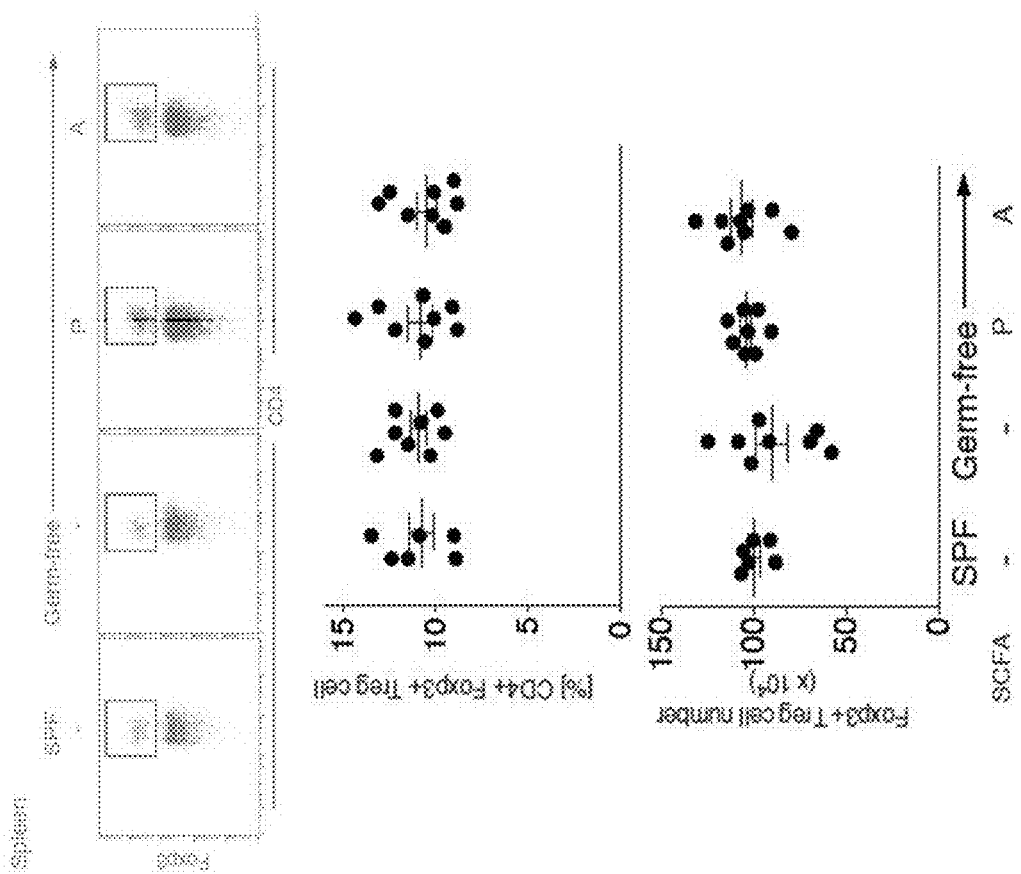
FIGS. 2A-2C illustrate that short chain fatty acids (SCFA) do not affect splenic, mesenteric lymph node (MLN) or thymic $Foxp3^+$ $T_{reg}$ populations in germ-free (GF) mice. Lymphocytes were isolated from the spleen (FIG. 2A), MLN (FIG. 2B) or thymus (FIG. 2C) and stained for CD4 and Foxp3. Upper panels: Representative flowgrams. Lower panels: Percentage of and number of $CD4^+Foxp3^+$ within the $CD45^+CD3^+$ population from SPF, GF, and GF mice treated with propionic acid (P), acetic acid (A) or butyric acid (B) in the drinking water per mouse colon, as indicated. Each symbol represents data from an individual mouse and data reflect 3-5 independent experiments. P-values are not shown as differences with SCFA treatment were not statistically significant. Horizontal lines show the mean and error bars the SD.
Figure 2B:
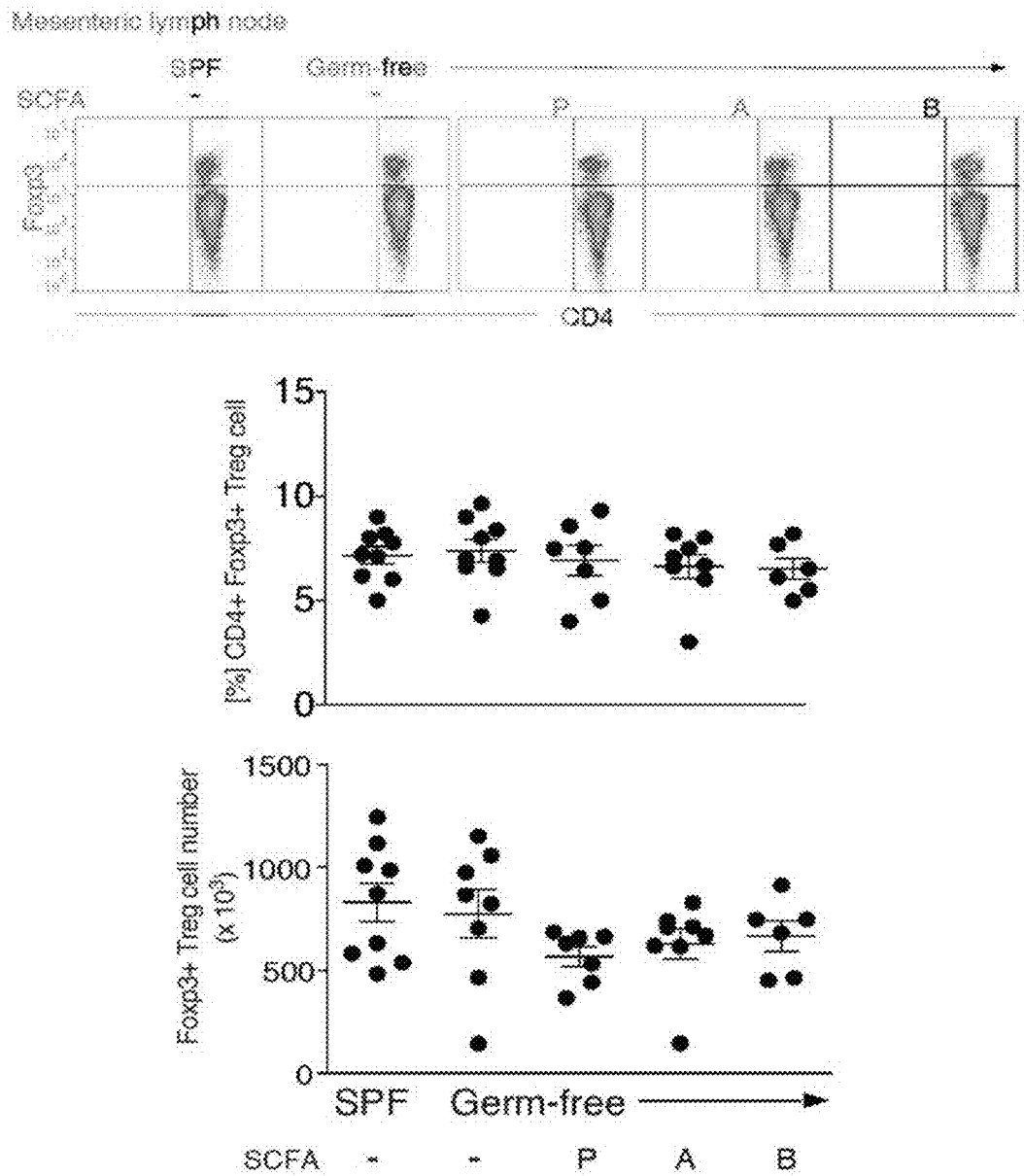
Figure 2C:
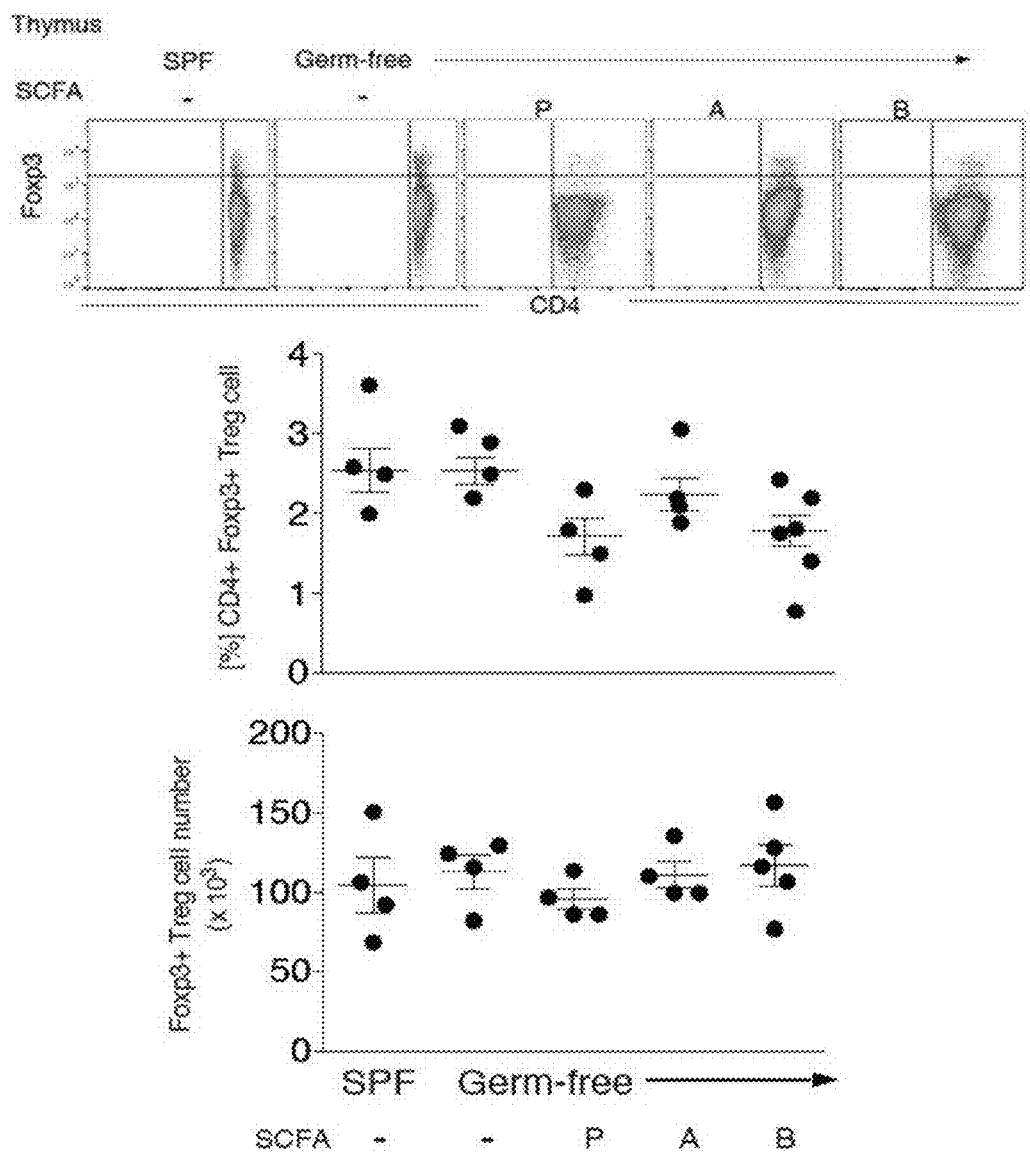
Figure 3:
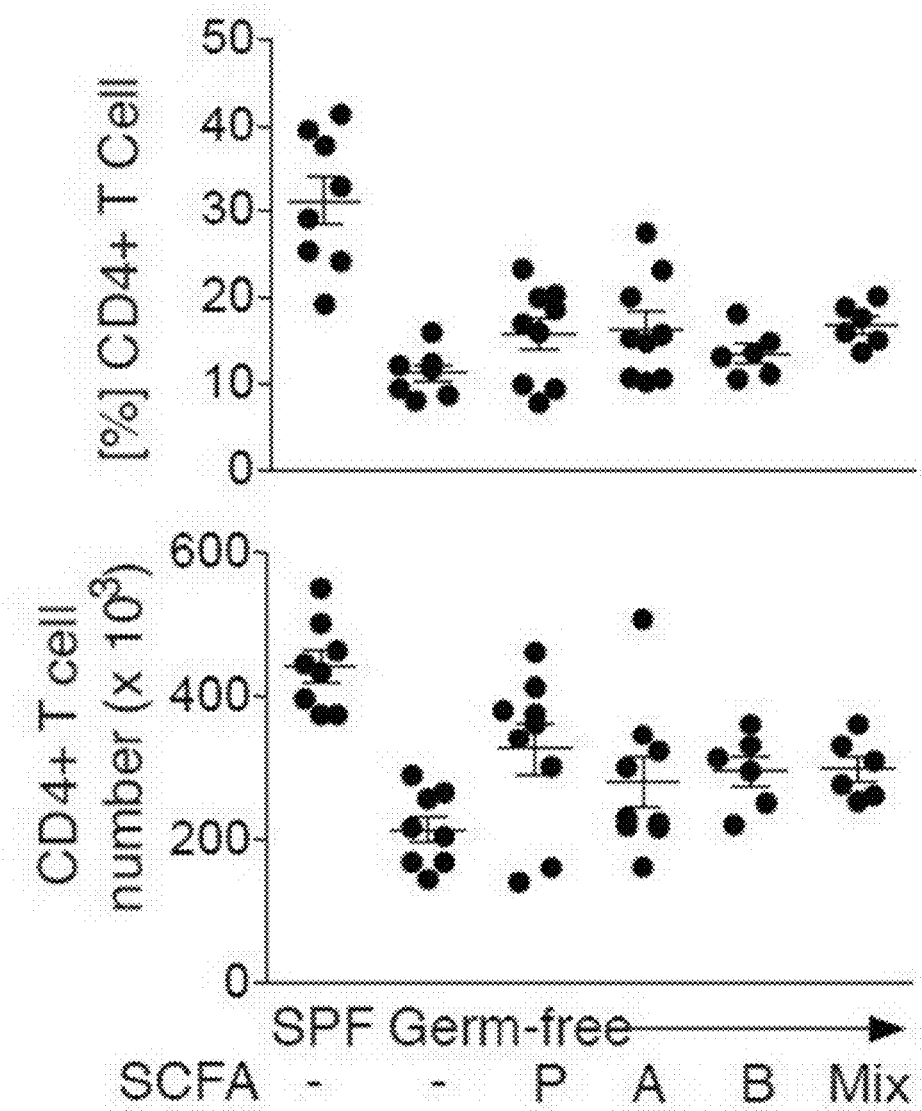
FIG. 3 shows that short chain fatty acids (SCFA) affect total colonic $CD4^+$ T cells. Lymphocytes were isolated from the colon and stained for CD4 and Foxp3. Upper panel: Percentage of, and Lower panel: Number of, $CD4^+$ within the $CD45^+CD3^+$ population from SPF, GF, and GF mice treated with propionic acid (P), acetic acid (A), butyric acid (B), or SCFA mix per mouse colon. Each symbol represents data from an individual mouse and the data reflect 3-5 independent experiments. P-values are not shown as differences with SCFA treatment were not statistically significant. Horizontal lines show the mean and error bars the SD.
Figures 4A, 4B, 4C, 4D:
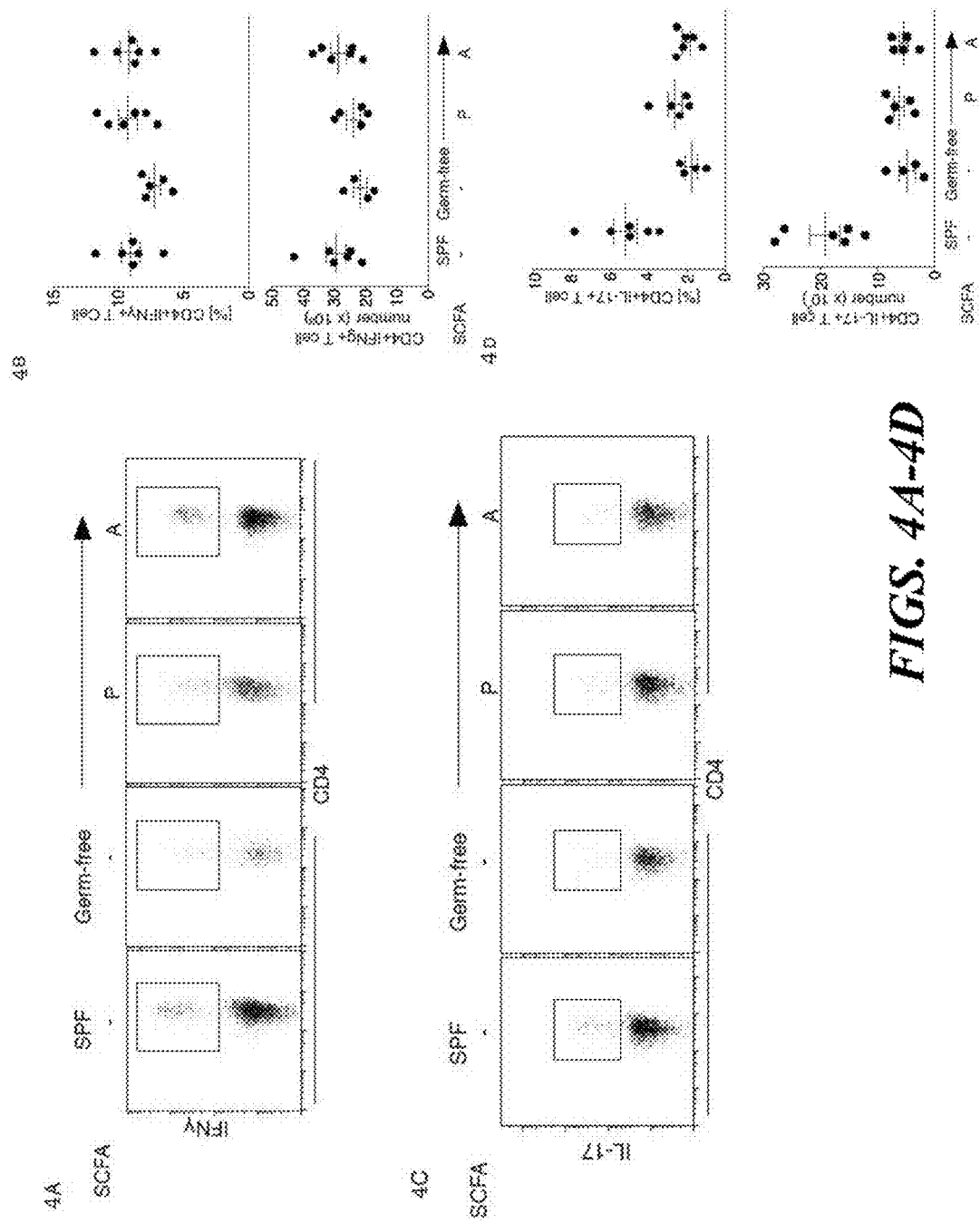
FIGS. 4A-4D illustrate that short chain fatty acids (SCFA) do not affect colonic Th1 and Th17 cells in germ-free (GF) mice. Lymphocytes were isolated from the colon of SPF, GF and GF mice treated with propionic acid (P) or acetic acid (A) in the drinking water for three weeks and stained for CD45, CD3, CD4, IFNγ, and IL-17.

The present investigators provided SCFA in the drinking water (150 mM) of GF mice for three weeks and, as depicted in FIG. 1B, observed that each SCFA individually or in combination (SCFA mix) significantly increased the percentage and number of $cT_{reg}$. The observed effects were restricted to the colon, as $T_{reg}$ numbers and frequency in the spleen, mesenteric lymph nodes (MLNs) and thymus were unchanged (FIGS. 2A, 2B and 2C). These effects coincided with increased luminal SCFA (Table 1). SCFA increased CD4+ T cell frequency and number (FIG. 3), but did not alter colonic Th1 or Th17 cell numbers significantly (FIG. 4).

Figure 1C:
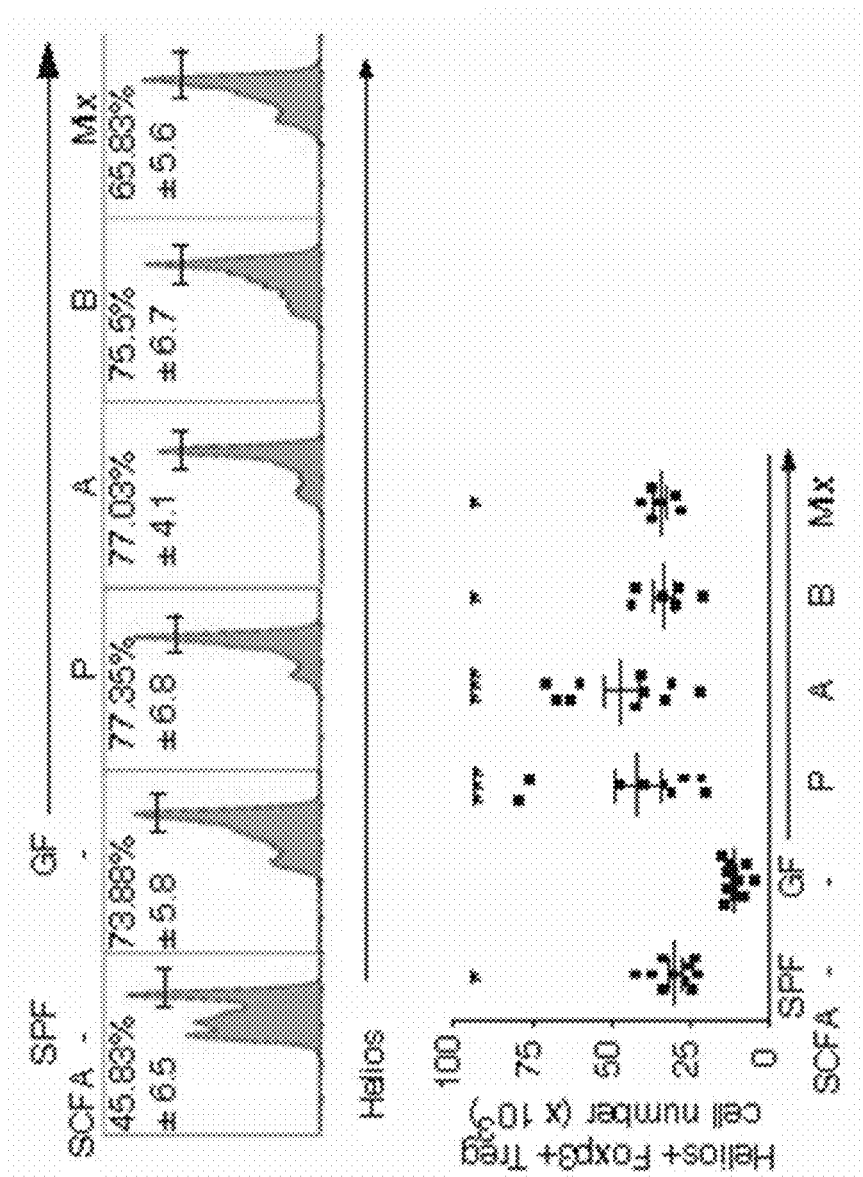
Figure 1D:
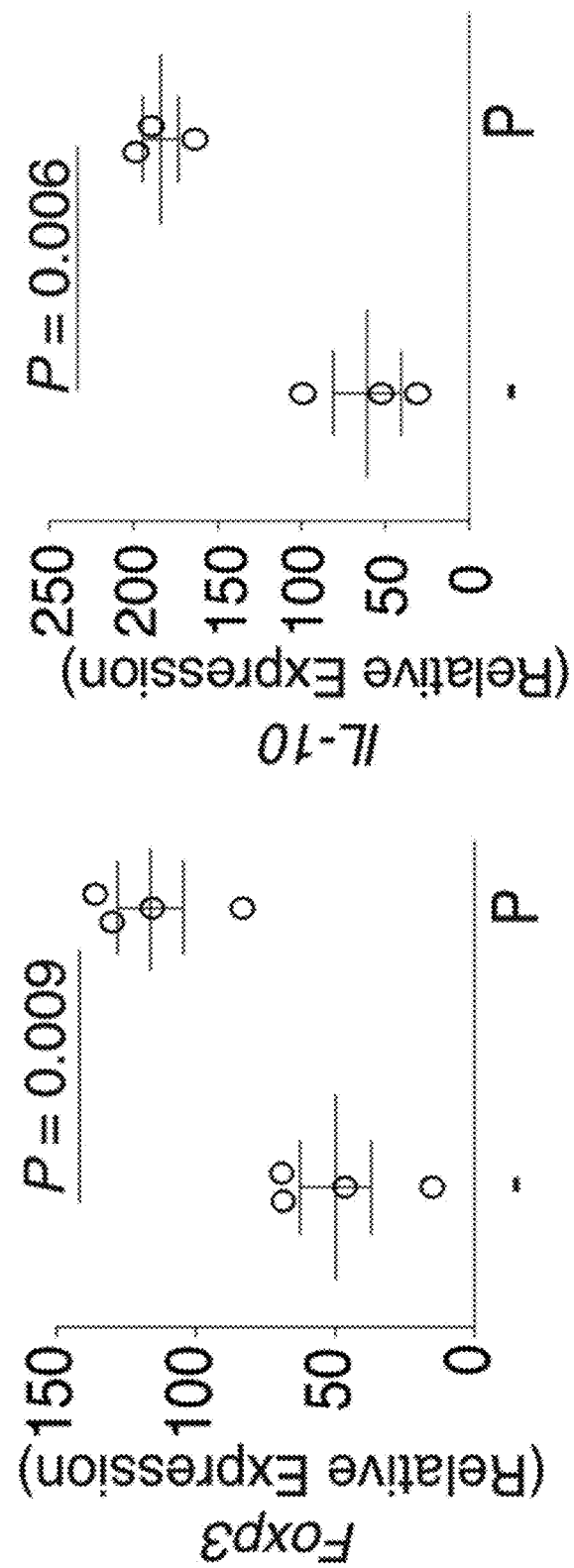
Figure 1E:
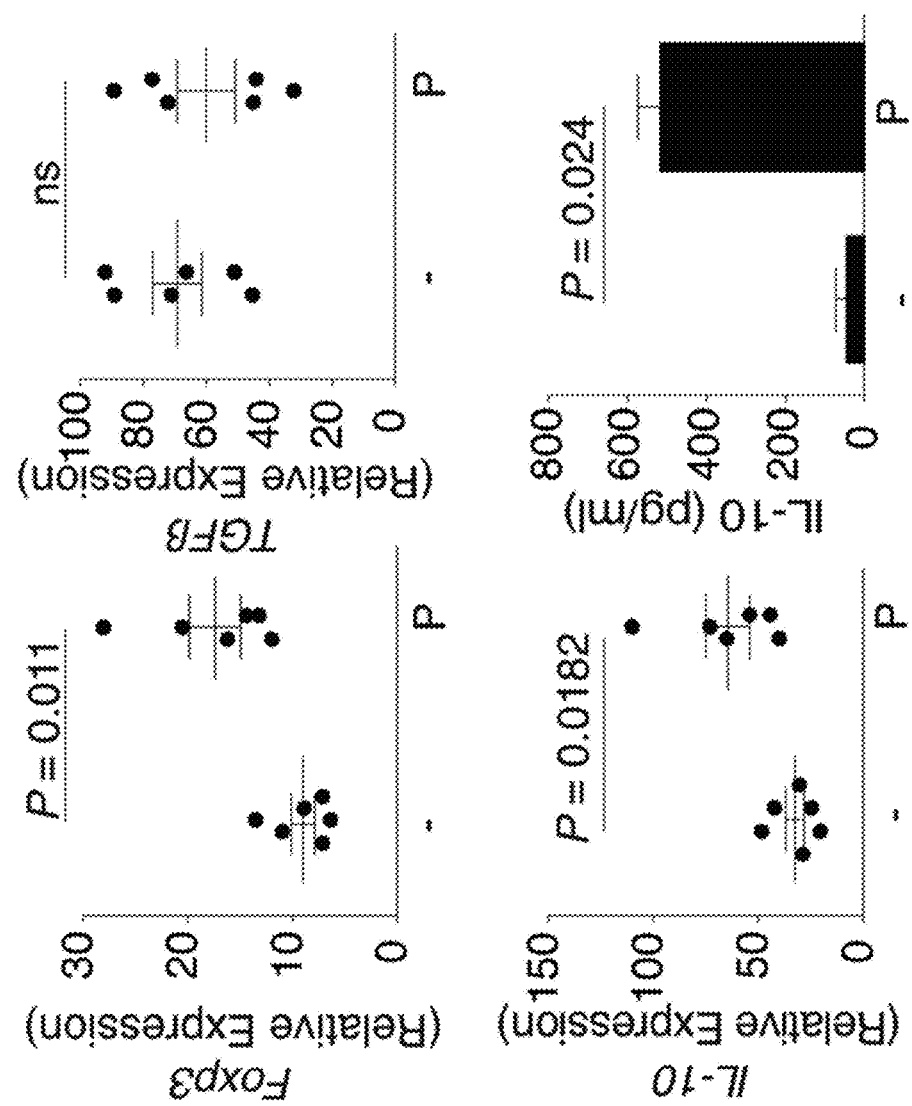

Microbiota-induced $cT_{reg}$ development is associated with an increase in de novo generation of inducible $T_{reg}$ ($iT_{reg}$) and not in $T_{reg}$ of thymic origin ($nT_{reg}$) (Atarashi, et al., *Science* 331, 337-341 (2011)). These two populations can be distinguished by their expression of the transcription factor Helios, which in vivo is restricted to $nT_{reg}$ (Thornton et al., *J. Immunol.* 184, 3433-3441 (2010)). As illustrated in FIG. 1C, the present investigators determined that the proportion of Helios$^+$ $T_{reg}$ remained unchanged between GF mice and GF mice treated with SCFA and was significantly greater than in SPF mice, indicating an expansion in $T_{reg}$ already present in the colonic lamina propria (cLP) rather than de novo generation.

and IL-10 expression, as shown in FIGS. 1D and 1E. In vitro treatment increased IL-10 production but not transforming growth factor-β (TGFβ) (FIGS. 1D and 1E), a $T_{reg}$-mediated suppression factor, suggesting that SCFA specifically induce Foxp3$^+$ IL-10 producing $T_{reg}$ subsets.

Figure 1F:
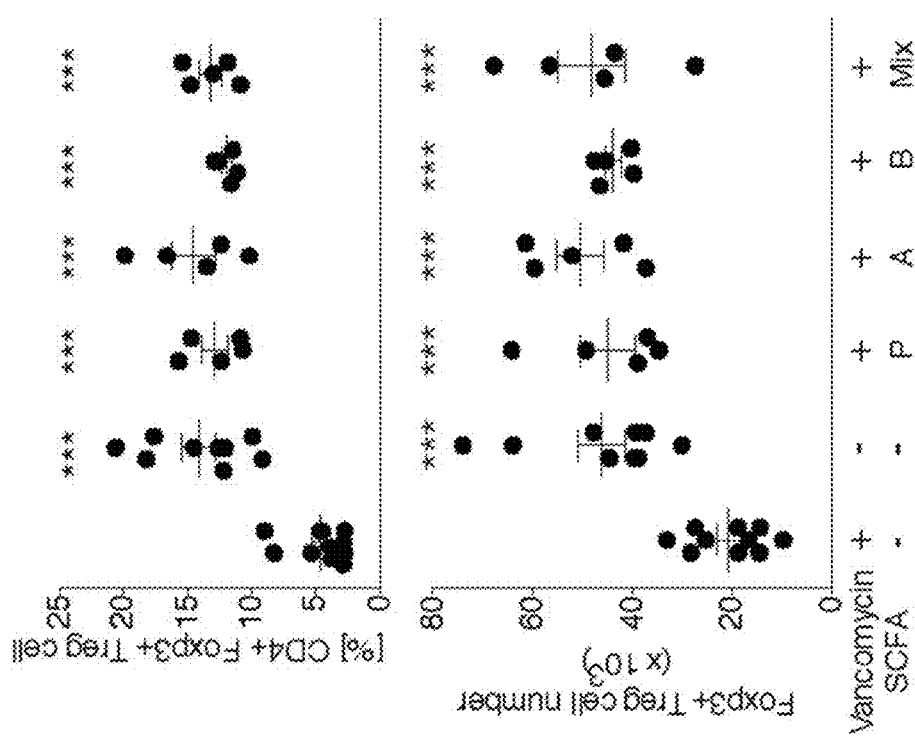

Exposure to the antibiotic vancomycin, which preferentially targets Gram-positive bacteria and disrupts the gut microbial community, reduced $cT_{reg}$ to similar levels as those observed in GF mice, as shown in FIG. 1F. However, when SPF mice were treated with a combination of vancomycin and SCFA, the reduction in $cT_{reg}$ was completely restored (FIG. 1F).

Collectively, the foregoing results provide evidence that SCFA play a critical role in $cT_{reg}$ homeostasis.

Example 2

Figure 5A:
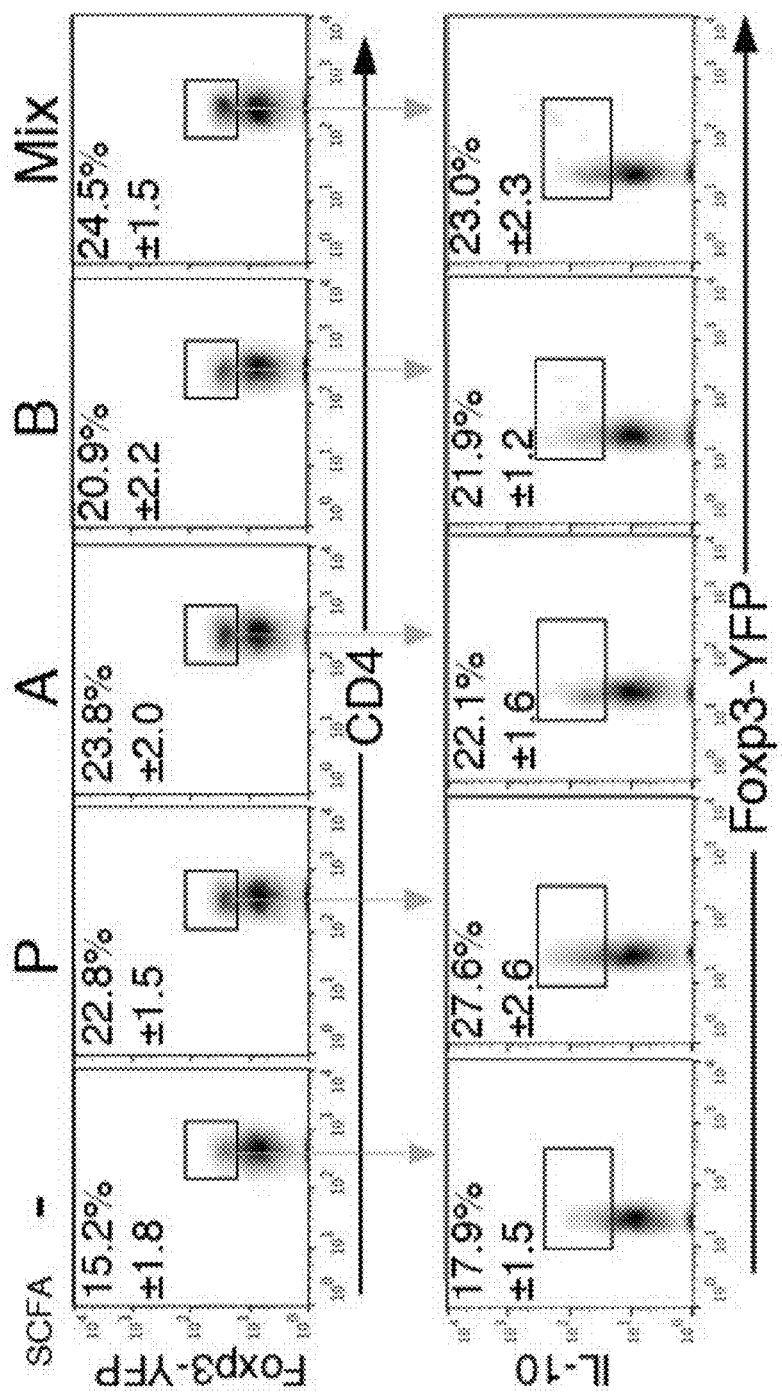
FIGS. 5A-5F illustrate that short chain fatty acids (SCFA) augment colonic $T_{reg}$ ($cT_{reg}$) population size and function in SPC mice.
Figure 5B:
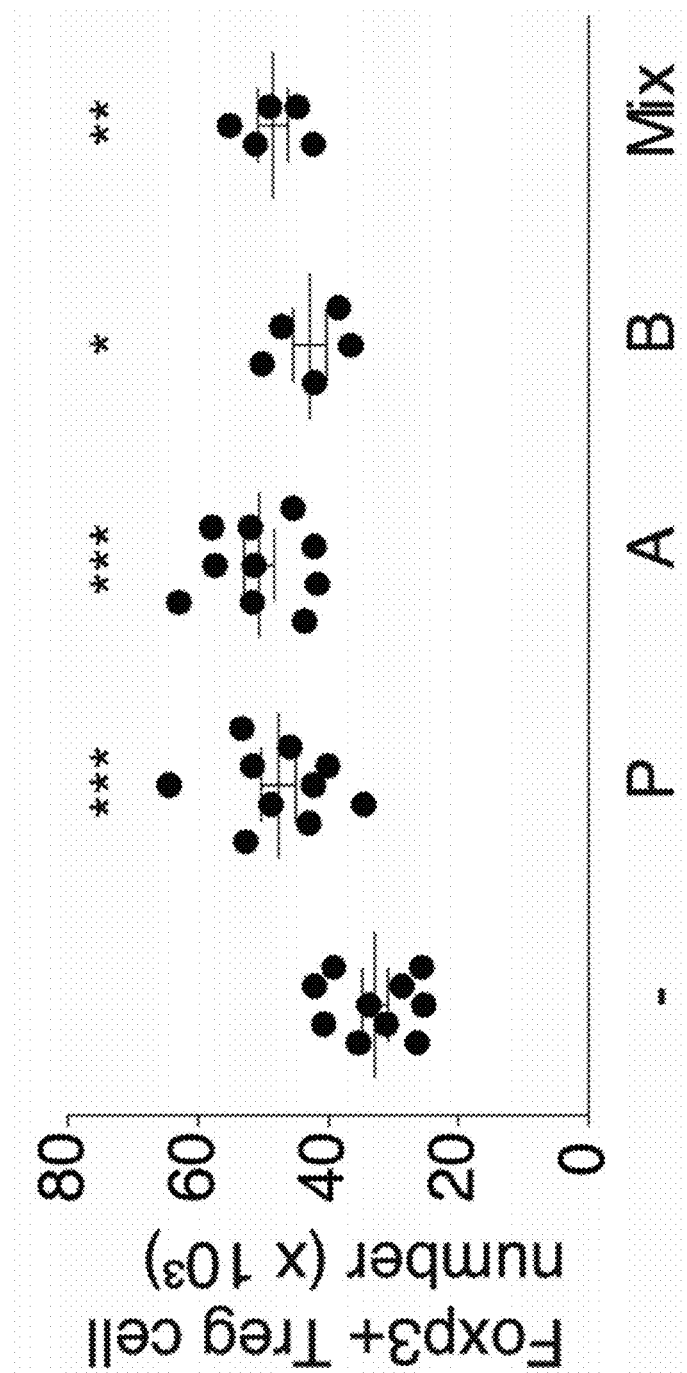
Figure 5C:
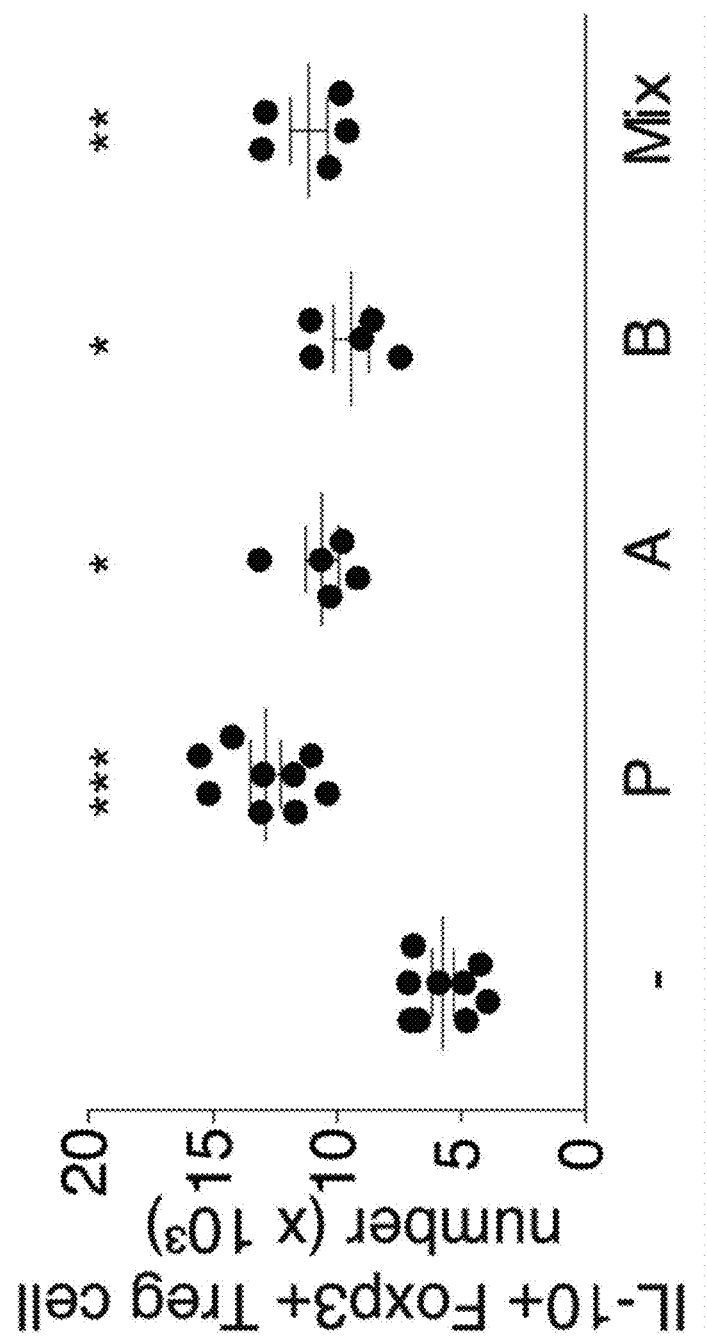
Figure 9:
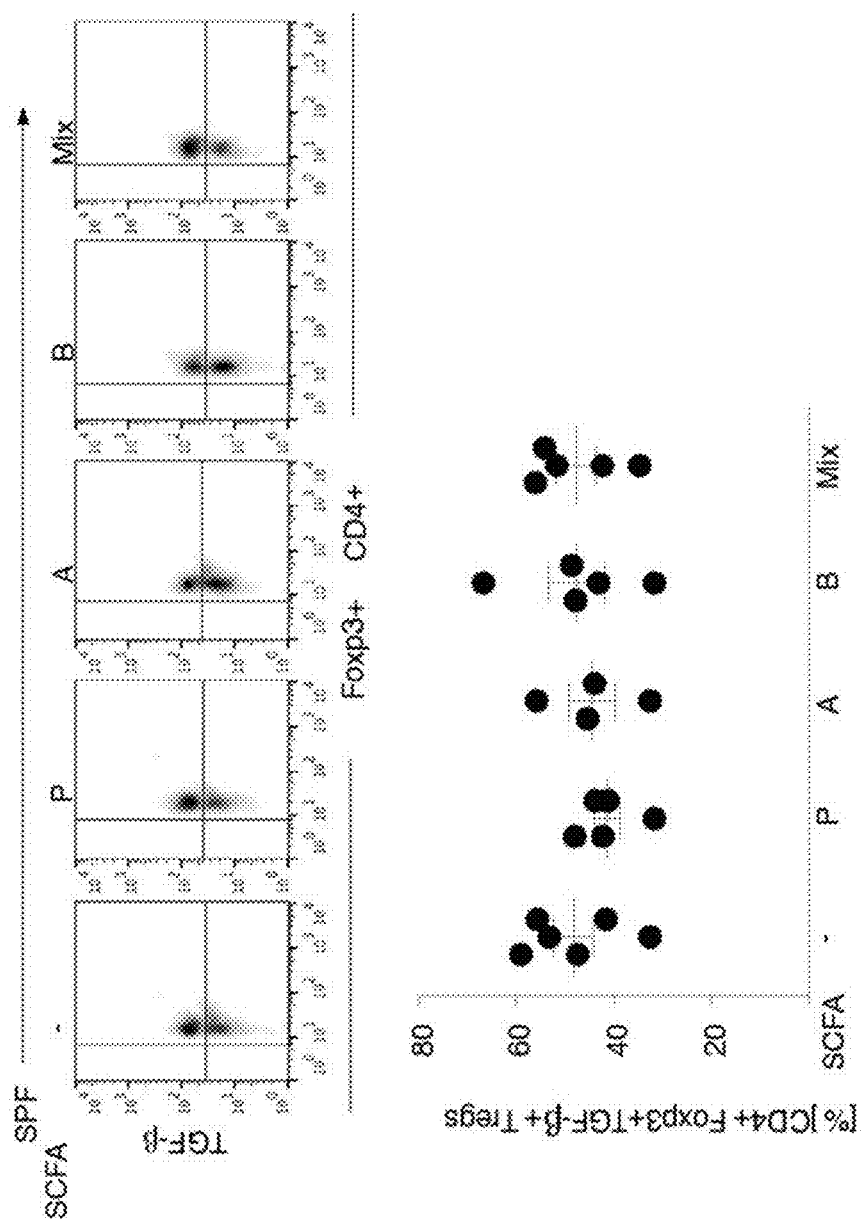
FIG. 9 illustrates that short chain fatty acids (SCFA) do not affect TGFβ levels of colonic Foxp3$^+$ T$_{reg}$ populations in SPF mice. BALB/c SPF mice were treated with pH and sodium-matched water alone (-), propionic acid (P), acetic acid (A) or butyric acid (B), or the SCFA mix in the drinking water for two weeks. Colonic lamina propria (LP) lymphocytes were isolated and stained for CD45, CD4, Foxp3, and TGF-β. Upper panel: Representative flowgrams. Lower panel: Percentage of CD4$^+$Foxp3$^+$ T$_{reg}$ expressing TGFβ within the CD45$^+$ population from all of the treatment groups. Each symbol represents data from an individual mouse and the data reflect 3 independent experiments. P-values are not shown as differences with SCFA treatment were not statistically significant. Horizontal lines represent the mean and error bars the SD.
Figure 10:
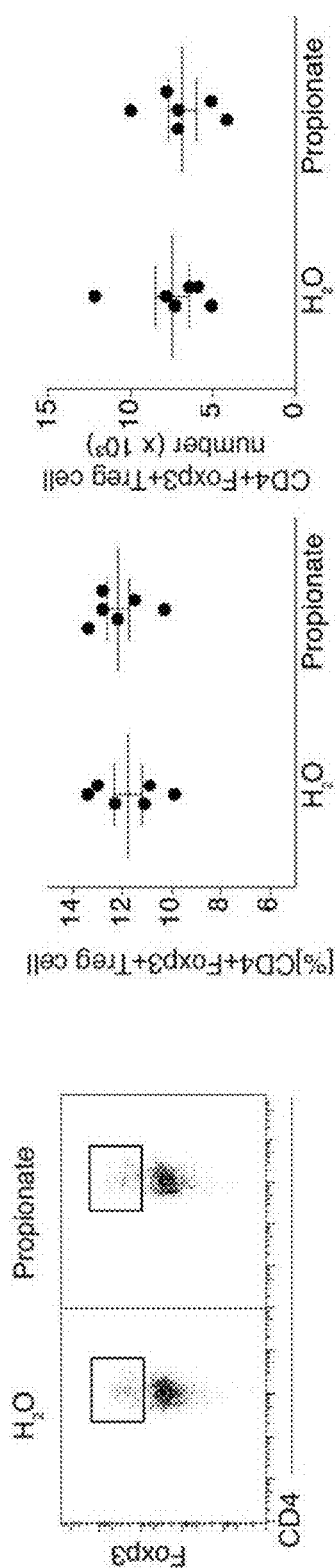
FIG. 10 illustrates that propionate does not affect small intestinal Foxp3$^+$ T$_{reg}$ populations in SPF mice. Lamina propria (LP) lymphocytes were isolated from the distal 10 cm of the ileum and stained for CD45, CD4, and Foxp3. Left panel: Representative flowgrams. Middle panel: Percentage of, and Right panel: Number of, CD4$^+$Foxp3$^+$ within the CD45$^+$ population from SPF mice treated with propionate or pH and sodium-matched water per mouse distal ileum. Each symbol represents data from an individual mouse and data reflect two independent experiments. P-values are not shown as differences with SCFA treatment were not statistically significant. Horizontal lines represent the mean and error bars the SD.

Having determined that SCFA can restore $cT_{reg}$ populations, further investigations were undertaken to determine whether SCFA could augment $cT_{reg}$ in SPF mice. As depicted in FIGS. 5A, 5B and 5C, treatment of SPF mice with individual SCFA or a mixture of SCFA increased the frequency and number of Foxp3$^+$ $cT_{reg}$ as well as Foxp3$^+$ IL-10$^+$ $cT_{reg}$, and SCFA did not affect Foxp3$^+$TGFβ$^+$ $cT_{reg}$ (FIG. 9). Changes were not observed with SCFA treatment in small intestinal $T_{reg}$ numbers, as illustrated in FIG. 10. To determine if SCFA effects have a broad impact on intestinal T cell populations, colonic Th17 and Th1 cells were also

TABLE 1

| | SCFA levels | | | | | | | |
|---|---|---|---|---|---|---|---|---|
| Cecal or Si contents | SPF | ASF | GF | GF + P | GF + A | GF + B | GF + Mic | SPF + P |
| μmol/g luminal contente | | | | | | | | |
| Propionate | 21.90 ± 0.122 | 18.83 ± 2.72 | 1.46 ± 0.162 | 14.93 ± 4.50 | — | — | 11.78 ± 6.38 | 43.33 ± 12.17 |
| Acetate | 40.66 ± 5.86 | 28.69 ± 8.32 | 2.82 ± 0.534 | — | 16.18 ± 4.65 | — | 20.83 ± 0.47 | — |
| Butyrate | 18.52 ± 4.92 | 16.89 ± 1.46 | 2.13 ± 0.598 | — | — | 11.46 ± 1.46 | 20.6 ± 3.96 | — |

| Cecal or Si contents | SPF + A | SPF + B | SPF + Vanco | SPF SI | SPF SI + P |
|---|---|---|---|---|---|
| μmol/g luminal contente | | | | | |
| Propionate | — | — | 1.851 ± 1.41 | 2.69 ± 0.24 | 12.08 ± 3.69 |
| Acetate | 53.95 ± 1.91 | — | 8.63 ± 1.73 | 15.19 ± 9.2 | 15.46 ± 3.69 |
| Butyrate | — | 29.78 ± 6.202 | 1.04 ± 0.903 | 7.183 ± 2.39 | 6.45 ± 2.11 |

| Select bacterial species | ASF 356 (XIV) | ASF 492 (XIV) | *Clostridium remosum* (XVII) | *Clostridium bifermentans* (XI) | *Bacteroides fragilis* |
|---|---|---|---|---|---|
| μmol/10^5 CFU | | | | | |
| Propionate | 62.39 ± 0.22 | 22.93 ± 0.109 | 14.74 ± 0.526 | 1.147 ± 0.008 | 0.0517 ± 0.001 |
| Acetate | 220.0 ± 0.435 | 123.2 ± 0.272 | 118.4 ± 0.526 | 1.973 ± 0.001 | 0.137 ± 0.001 |
| Butyrate | ND | ND | ND | ND | ND |

| SCFA mix in mouse water bottle over time | Input (Day 0) | Day 1 | Day 4 | Day 7 | Day 10 | Day 14 | Day 90 |
|---|---|---|---|---|---|---|---|
| mM | | | | | | | |
| Propionate | 200 | 200 | 199.6 | 201.24 | 202.9 | 203.2 | 41.9 |
| Acetate | 200 | 195 | 220.1 | 192.2 | 196.3 | 202.5 | 56.1 |
| Butyrate | 200 | 203.09 | 202.85 | 202.27 | 202.69 | 202.19 | 38 |

Figure 11:
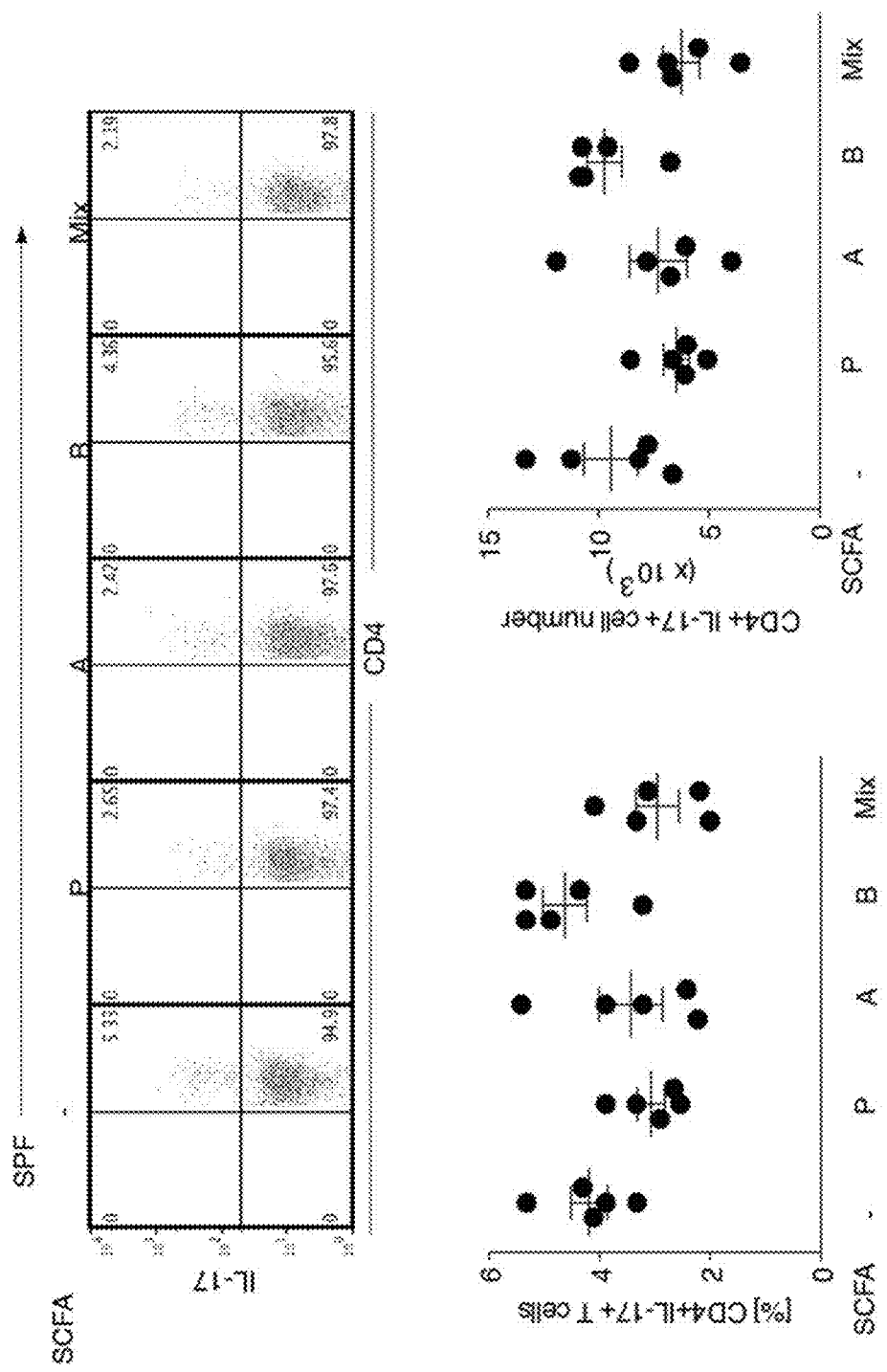
FIG. 11 shows that short chain fatty acids (SCFA) do not affect colonic Th17 populations in specific pathogen-free (SPF) mice. BALB/c SPF mice were treated with pH and sodium-matched water alone (-), propionic acid (P), acetic acid (A) or butyric acid (B), or the SCFA mix. Colonic lamina propria (LP) lymphocytes were isolated and stained for CD45, CD4, Foxp3, and IL-17. Upper panel: Representative flowgrams. Lower left panel: Percentage of Foxp3- CD4$^+$ T cells expressing IL-17 per mouse colon. Lower right panel: Number of Foxp3-CD4$^+$ T cells expressing IL-17 per mouse colon. Symbols represent data from individual mice. Data reflect three-five independent experiments. P-values are not shown as differences with SCFA treatment were not statistically significant. Horizontal lines represent the mean and error bars the SD.
Figure 12:
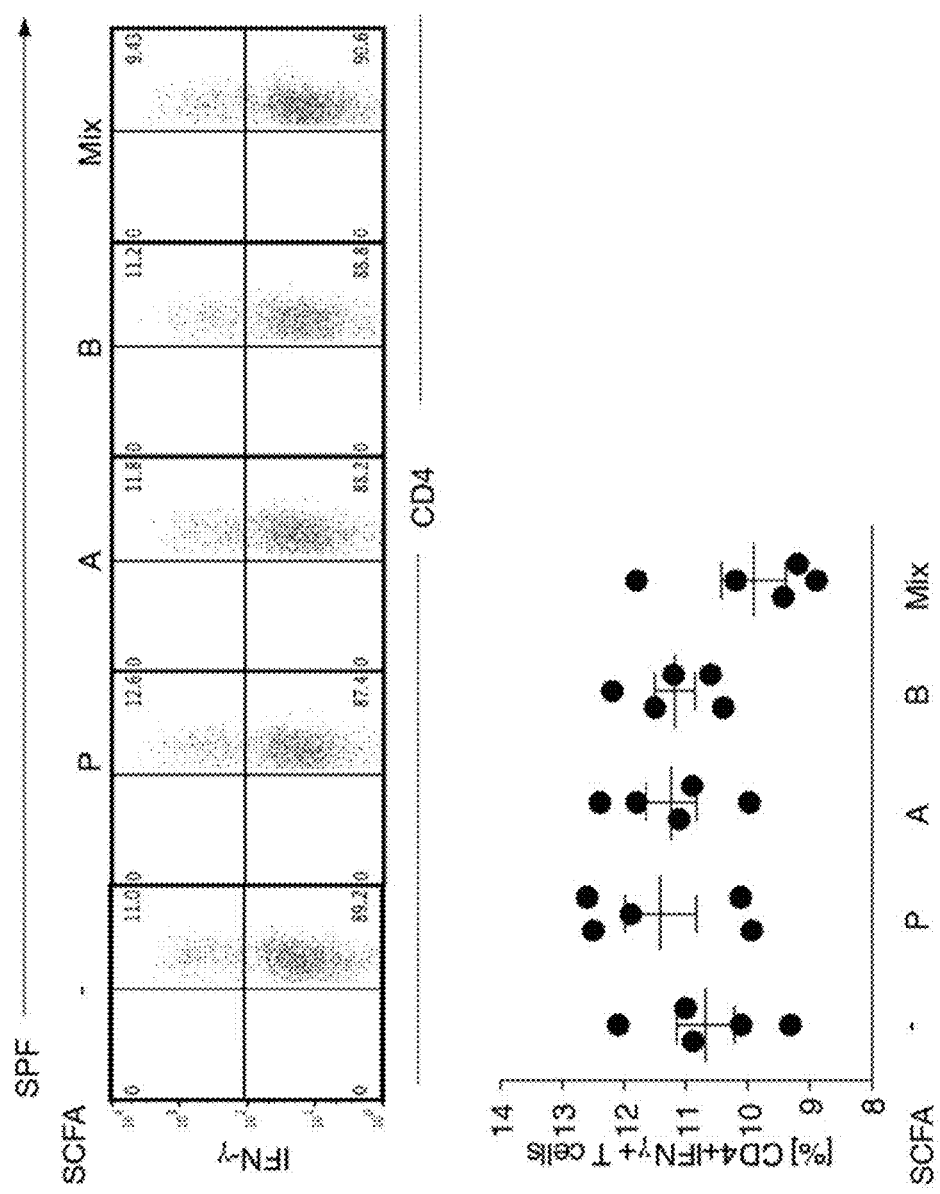
FIG. 12 illustrates that short chain fatty acids (SCFA) do not affect colonic Th1 populations in specific pathogen-free (SPF) mice. BALB/c SPF mice were treated with pH and sodium-matched water alone (-), propionic acid (P), acetic acid (A) or butyric acid (B), or the SCFA mix. Colonic lamina propria (LP) lymphocytes were isolated and stained for CD45, CD4, and IFNγ. Upper panel: Representative flowgrams. Lower panel: Percentage of CD4$^+$ T cells expressing IFNγ within the CD45$^+$ population from all of the treatment groups. Symbols represent data from individual mice and reflect data from three independent experiments. P-values are not shown as differences with SCFA treatment were not statistically significant. Horizontal lines represent the mean and error bars the SD.
Figure 13:
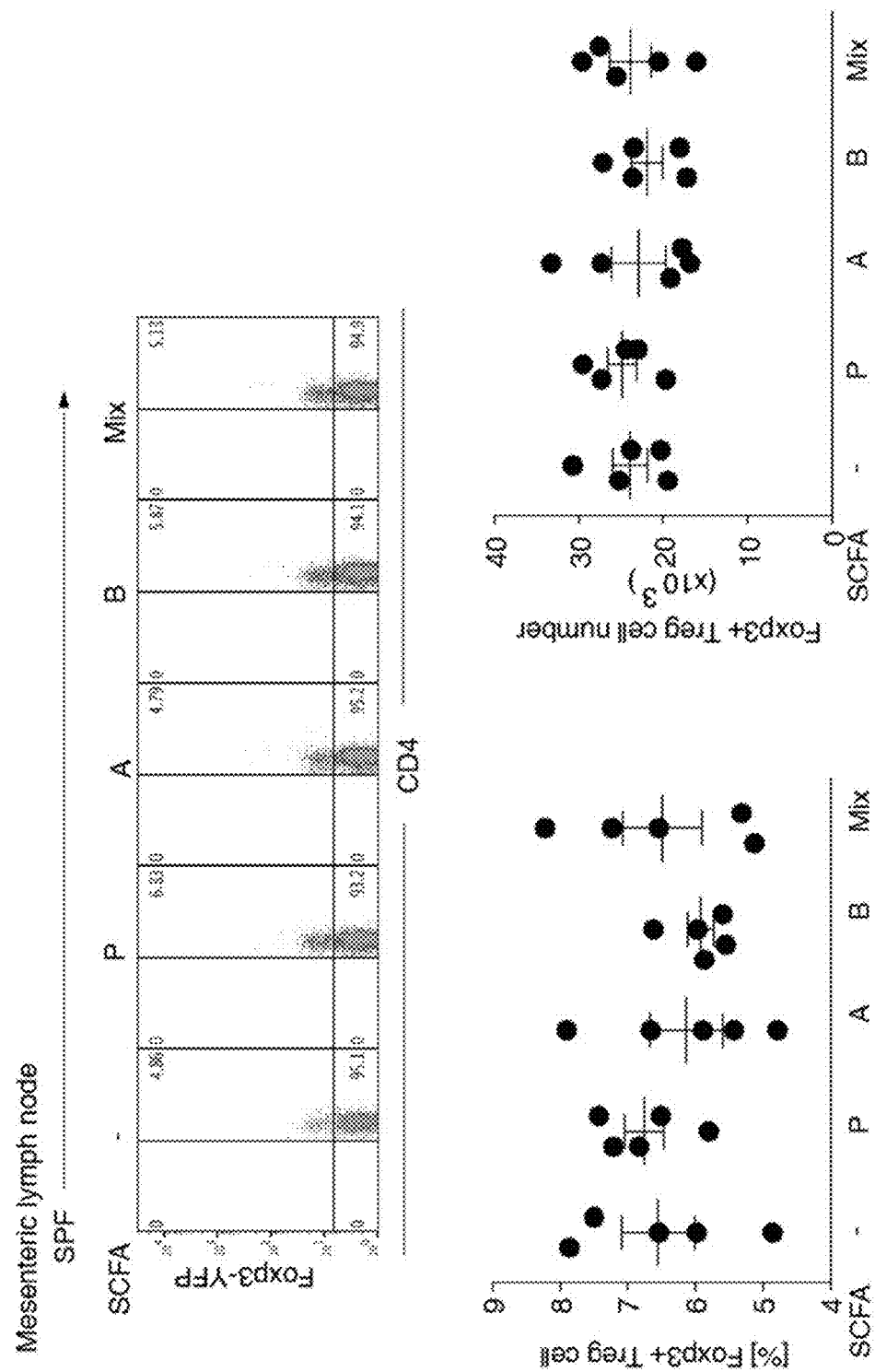
FIG. 13 illustrates that short chain fatty acids (SCFA) do not affect mesenteric lymph node (MLN) Foxp3$^+$ T$_{reg}$ populations in specific pathogen-free (SPF) mice. Lymphocytes were isolated from the MLNs of BALB/c SPF mice treated with pH and sodium-matched water alone (-), propionic acid (P), acetic acid (A) or butyric acid (B), or the SCFA mix and stained for CD45, CD4, and Foxp3. Upper panel: Representative flowgrams. Lower Left panel: Percentage of, and Lower right panel: Number of, CD4$^+$Foxp3$^+$ within the CD45$^+$ population. Symbols represent data from individual mice and reflect data from three independent experiments. P-values are not shown as differences with SCFA treatment were not statistically significant. Horizontal lines represent the mean and error bars the SD.
Figure 14:
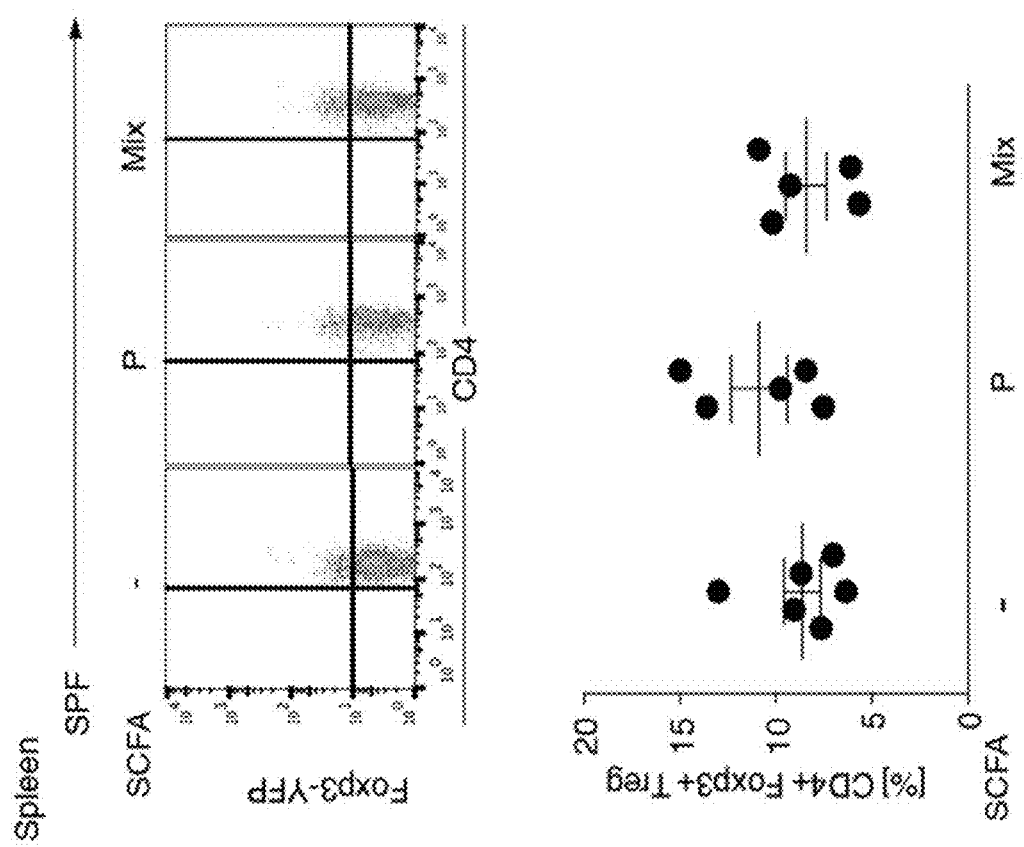
FIG. 14 illustrates that short chain fatty acids (SCFA) do not affect splenic Foxp3$^+$ T$_{reg}$ populations in specific pathogen-free (SPF) mice. Lymphocytes were isolated from the spleen of BALB/c SPF mice treated with pH and sodium-matched water alone (-), propionate (P), or the SCFA mix (Mix) and stained for CD45, CD4, and Foxp3. Upper panel: Representative flowgrams. Lower panel: Percentage of CD4$^+$Foxp3$^+$ within the CD45$^+$ population. Symbols represent data from individual mice and reflect data from two independent experiments. P-values are not shown as differences with SCFA treatment were not statistically significant. Horizontal lines represent the mean and error bars the SD.

To determine whether SCFA could directly affect $cT_{reg}$ in a GF setting, the present investigators isolated $cT_{reg}$ from GF mice treated with propionate in vivo for three weeks and examined expression of Foxp3 and interleukin 10 (IL-10), a key cytokine in $T_{reg}$-mediated suppression. The present investigators also isolated $cT_{reg}$ from GF mice and stimulated them with propionate for 24 hours in vitro. Both treatments resulted in a significant increase in both Foxp3 examined, however no significant changes were evident (FIGS. 11 and 12). Furthermore, SCFA did not alter $T_{reg}$ numbers in the MLN (FIG. 13) or the spleen (FIG. 14) of SPF mice. Thus SCFA specifically increase $cT_{reg}$ numbers in healthy mice with a conventional microbiota.

These results may explain the benefits of dietary fibers and bacteria, such as clostridia and bifidobacteria that can increase colonic luminal SCFA production and modulate inflammation in mice and humans. The present investigators measured SCFA production of species belonging to *Clostridium* cluster XI (*Clostridium bifermentans*), XIV (ASF 356 and 492), XVII (*C. ramosum*), and the bacteroides species, *B. fragilis* as *Clostridium* cluster XIV members and *B. fragilis* affect $cT_{regs}$. As shown in Table 1, ASF 356 and 492 and *C. ramosum* generated more propionate (14-62 vs 0.05-1.1 µmol/$10^5$ CFU) and acetate (118-220 vs 0.1-2 µmol/$10^5$ CFU) as compared to the other strains.

Figure 5D:
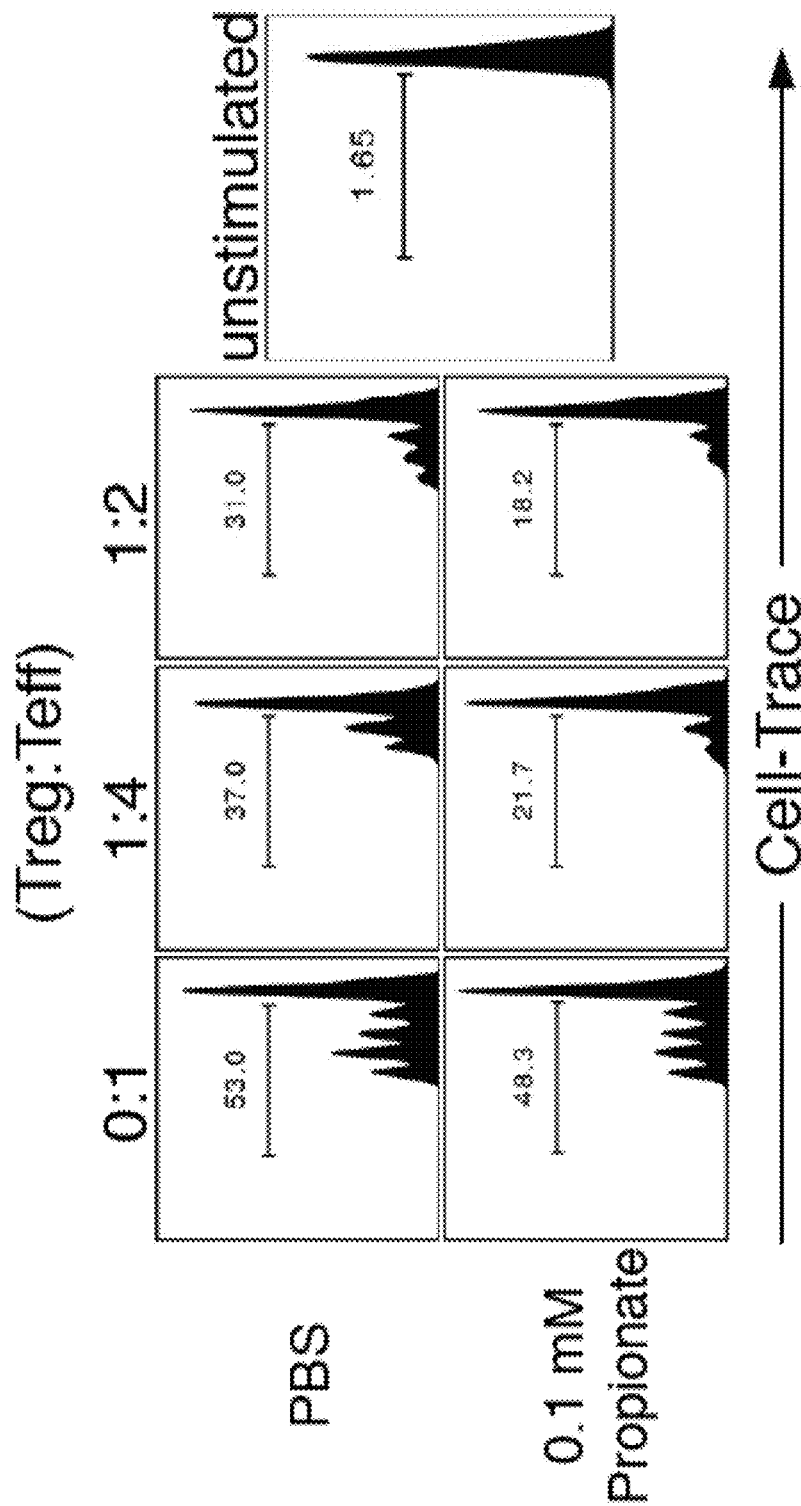
Figure 5E:
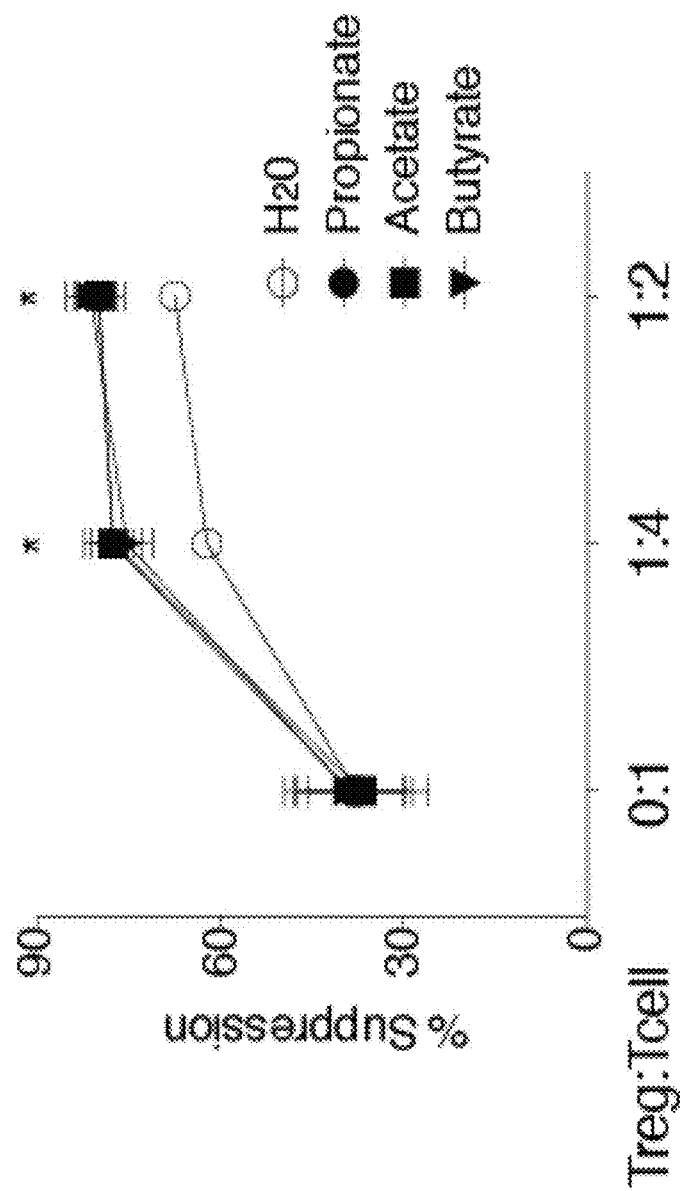

A major mechanism by which $T_{reg}$ regulate intestinal homeostasis and control inflammation is through their ability to limit proliferation of effector CD4+ T cells ($T_{eff}$). The addition of SCFA to $cT_{reg}$ and $T_{eff}$ co-cultures increased the in vitro suppressive capacity of $cT_{reg}$, as shown in FIGS. 5D and 5E, indicating that these SCFA enhance not only $cT_{reg}$ numbers but also their functional capacity.

Figure 5F:
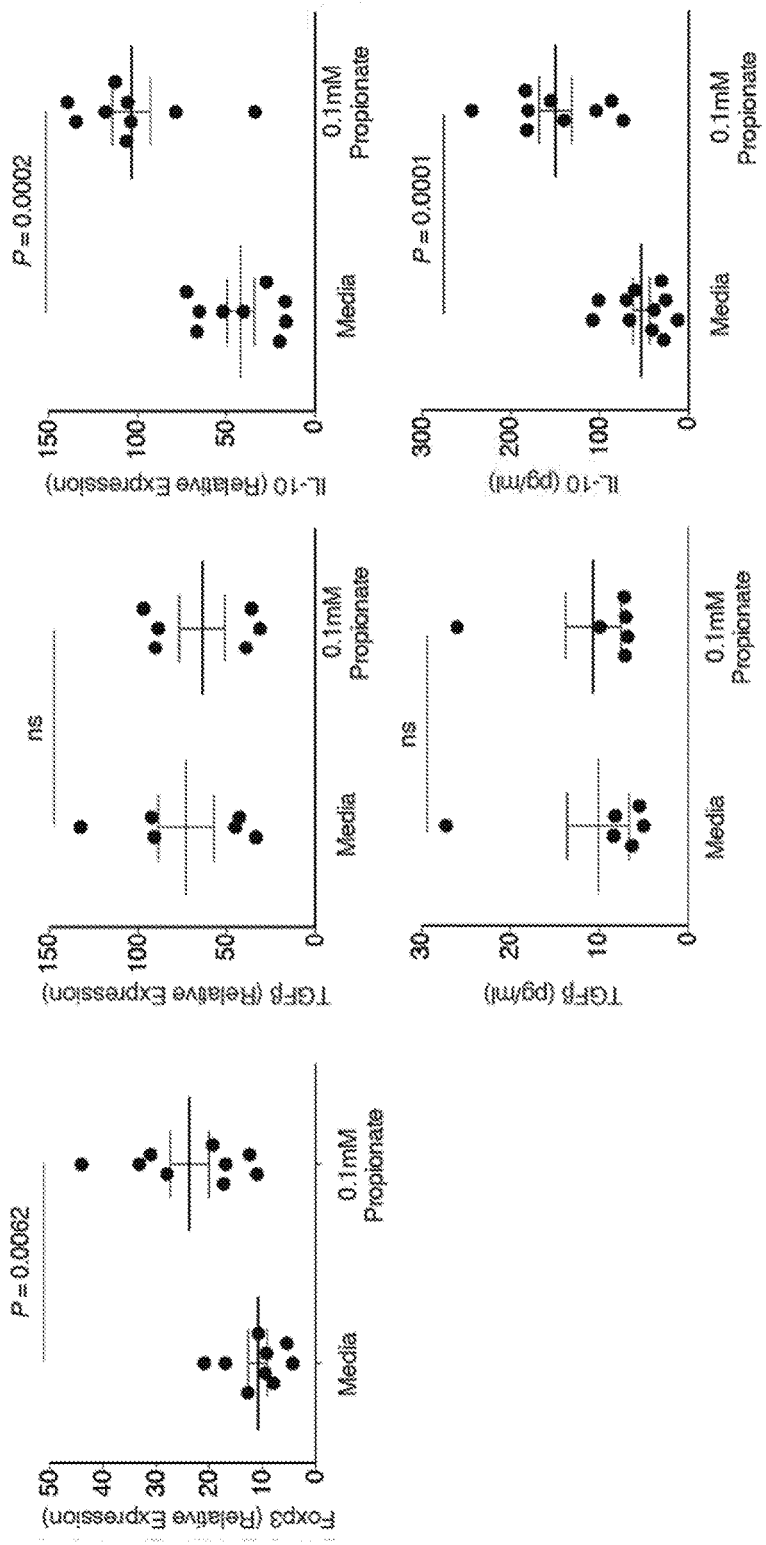
Figure 6:
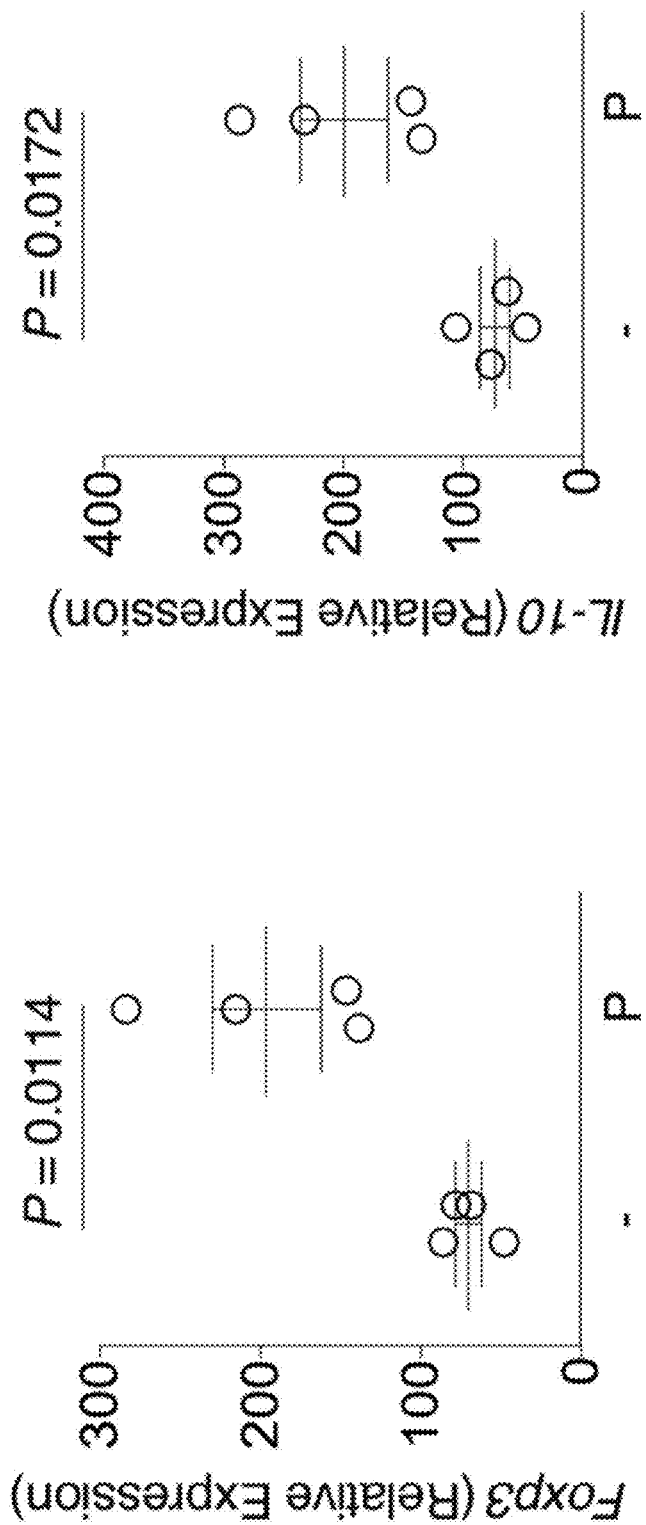
FIG. 6 illustrates the relative expression of Foxp3 and IL-10 from $cT_{reg}$ isolated from the lamina propria (LP) of in vivo propionate treated SPF Foxp3$^{YFP-Cre}$ mice, sorted for CD4 and YFP. Each symbol represents pooled cT$_{reg}$ from 3-5 mice, horizontal lines show the mean and error bars the SD. Four independent experiments were performed. A Mann-Whitney U test was performed and P-values are shown.

In SPF mice, SCFA are taken up by colonic epithelial cells but also diffuse through the epithelial cell layer into the lamina propria where they can mediate their effects directly. To determine if SCFA directly affect $cT_{reg}$, $cT_{reg}$ were isolated from SCFA-treated SPF mice. In vivo treatment increased $cT_{reg}$ Foxp3 and IL-10 expression (FIG. 6). $cT_{reg}$ were also isolated from SPF mice and incubated with SCFA for 24 hours in vitro. As illustrated in FIG. 5F, Foxp3 expression and IL-10 expression and protein production all increased. Incubation with SCFA did not alter $cT_{reg}$ TGFβ levels (FIG. 5F).

Figure 7:
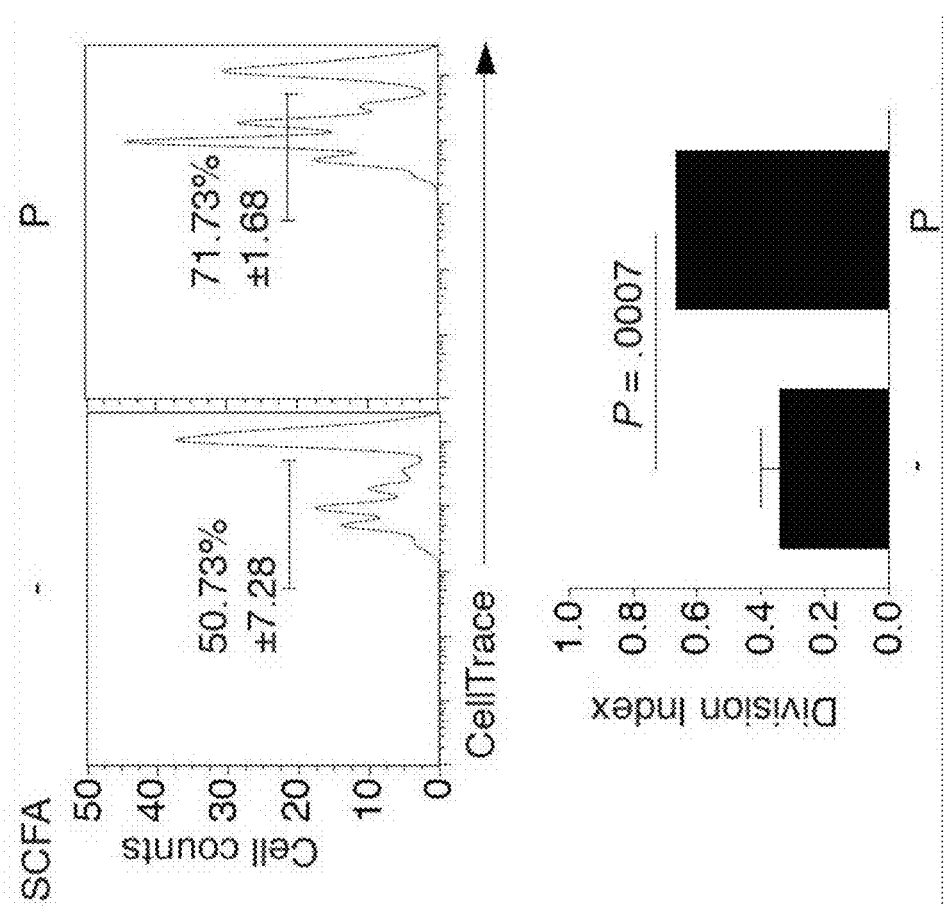
FIG. 7 shows that treatment with propionate enhances proliferation of colonic T$_{reg}$ (cT$_{reg}$). CD4$^+$ Foxp3-YFP$^+$ colonic T$_{reg}$ were FACS sorted, labeled with CellTrace cell violet (5 µM) and cultured with 1 µg/ml anti-CD3 and 500 ng/ml IL-2 in the presence or absence of 0.1 mM propionate. Histograms showing cell division are shown in the upper panel with average percentage of divided population ±SD on the histogram. Division index is plotted for the experimental conditions in the lower panel. Data are representative of two independent experiments. Student's t-test was performed to determine statistical significance. Horizontal lines represent the mean and error bars the SD.

As enhanced suppressive activity could be attributed not only to higher IL-10 levels per $cT_{reg}$, but also to increased $cT_{reg}$ proliferation, the present investigators examined $cT_{reg}$ proliferation. As illustrated in FIG. 7, $cT_{reg}$ exhibited enhanced proliferation when cultured in the presence of propionate.

Taken together, the foregoing results indicate that SCFA may have a beneficial effect in healthy SPF mice and perhaps humans through their ability to directly increase Foxp3+IL-10 producing $cT_{reg}$.

Example 3

Figure 8:
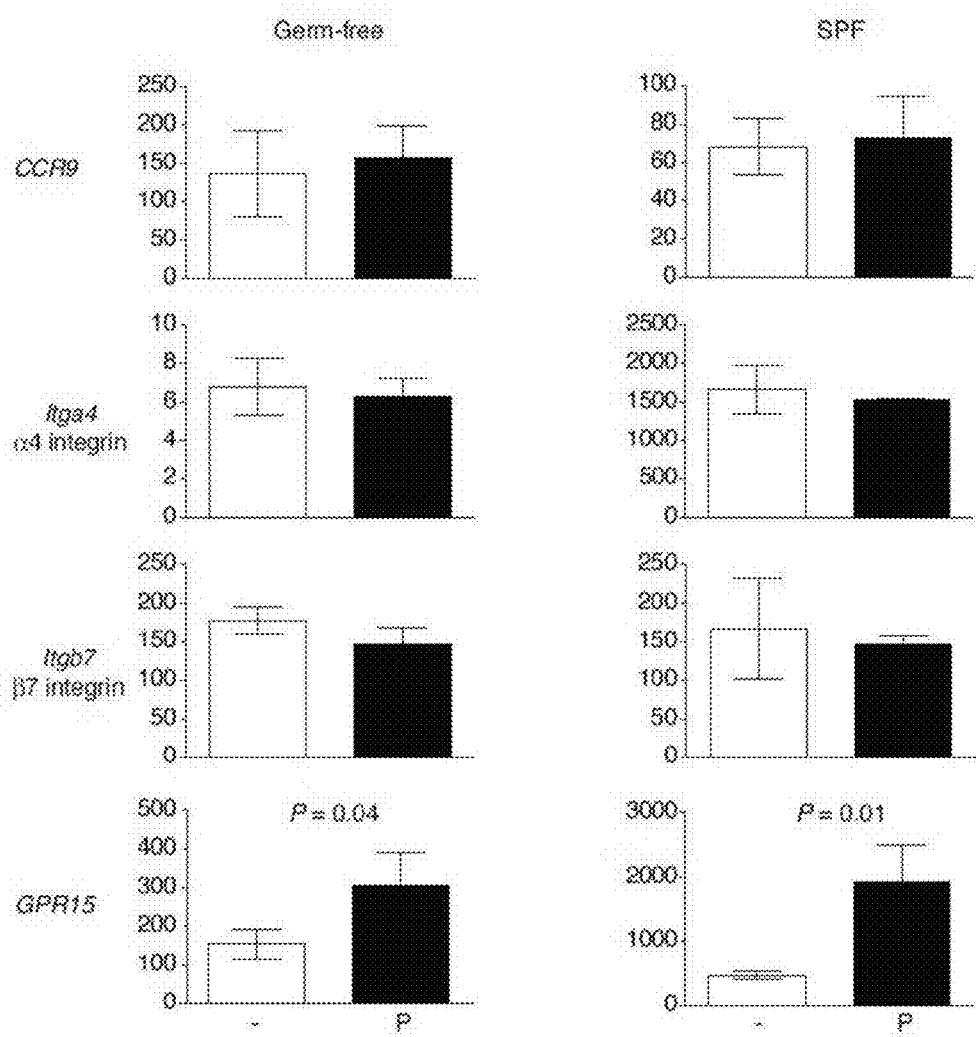
FIG. 8 presents chemokine receptor expression in colonic T$_{reg}$ from water vs. propionate-treated germ-free (GF) and specific pathogen-free (SPF) mice. Colonic lamina propria (LP) T$_{reg}$ were isolated from water or in vivo propionate-treated Swiss Webster GF (left panels) or SPF Foxp3$^{YFP-Cre}$ (right panels) mice and the ex vivo expression of the chemokine receptors CCR9, α4 integrin, β7 integrin and GPR15 were measured by RTqPCR. Data consist of 5 pooled mice per group and are representative of two independent experiments. Student's t-test was performed to determine significance. Error bars represent SD.

In view of the findings that SCFA can directly influence $cT_{reg}$, further investigations were performed to analyze the expression patterns of $T_{reg}$ trafficking molecules. Although levels of the chemokine receptor CCR9 or α4β7 integrin were not altered in propionate treated GF and SPF mice, levels of the $cT_{reg}$ homing receptor GPR15 did increase, as illustrated in FIG. 8. Taken together, these data indicate that SCFA may have a beneficial effect in SPF mice through their ability to increase Foxp3+IL-10 producing $cT_{reg}$ and $cT_{reg}$ proliferative capacity, as well as alter $cT_{reg}$ GPR15 expression.

Considering that SCFA can influence $cT_{reg}$ directly, further investigations were conducted to determine whether the observed influence was a receptor-mediated process. The G-coupled protein receptor 43 (GPR43), which is encoded by the Ffar2 gene, specifically binds SCFA and through its expression on innate immune cells mediates resolution of inflammatory responses (Maslowski et al., *Nature* 461, 1282-1286 (2009); Nilsson, et al., *Biochem. Biophys. Res. Commun.* 303, 1047-1052 (2003)). However, the role of Ffar2 and GPR43 in $T_{reg}$ cell development and function heretofore has not been probed.

Figure 15A:
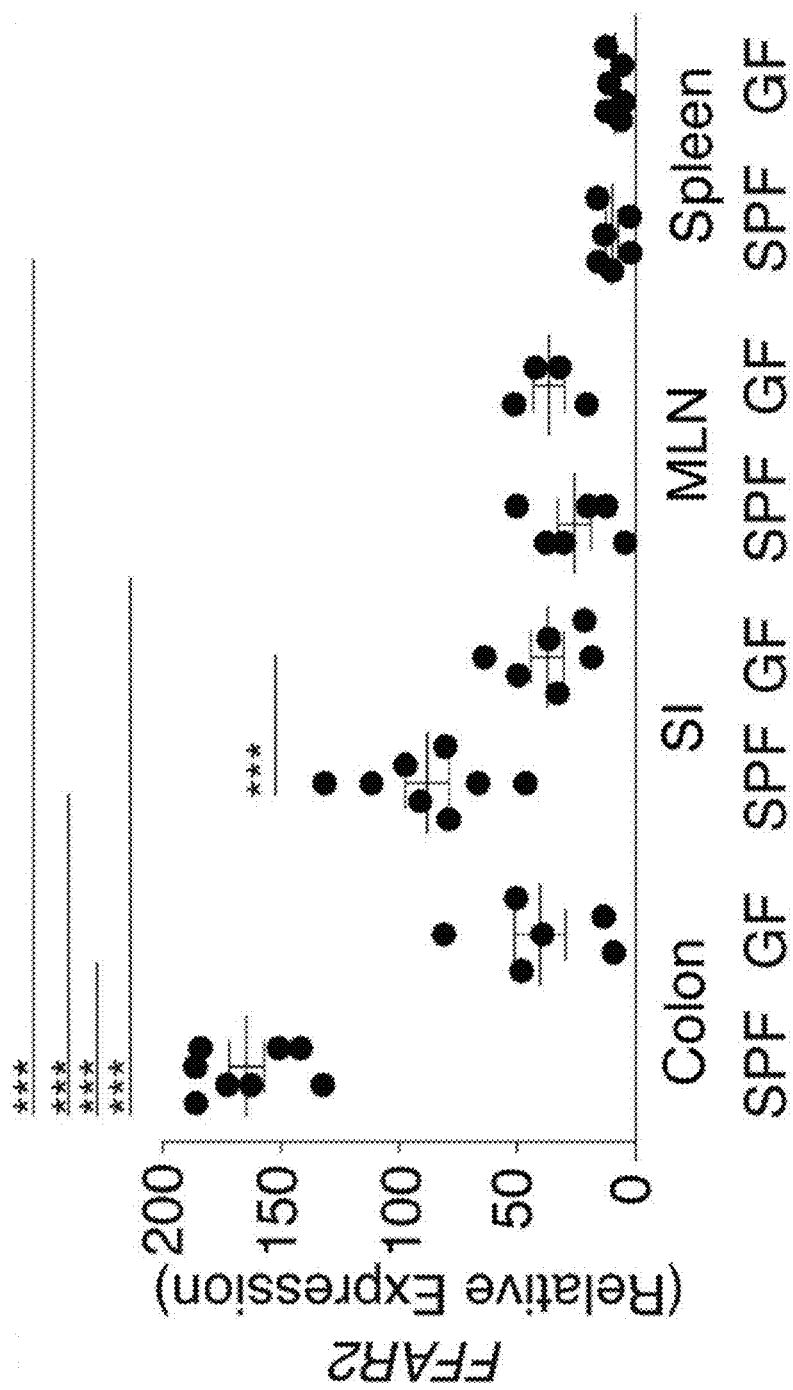
FIGS. 15A-15I show that Ffar2 mediates SCFA effects on colonic T$_{reg}$ (dT$_{reg}$).
Figure 15B:
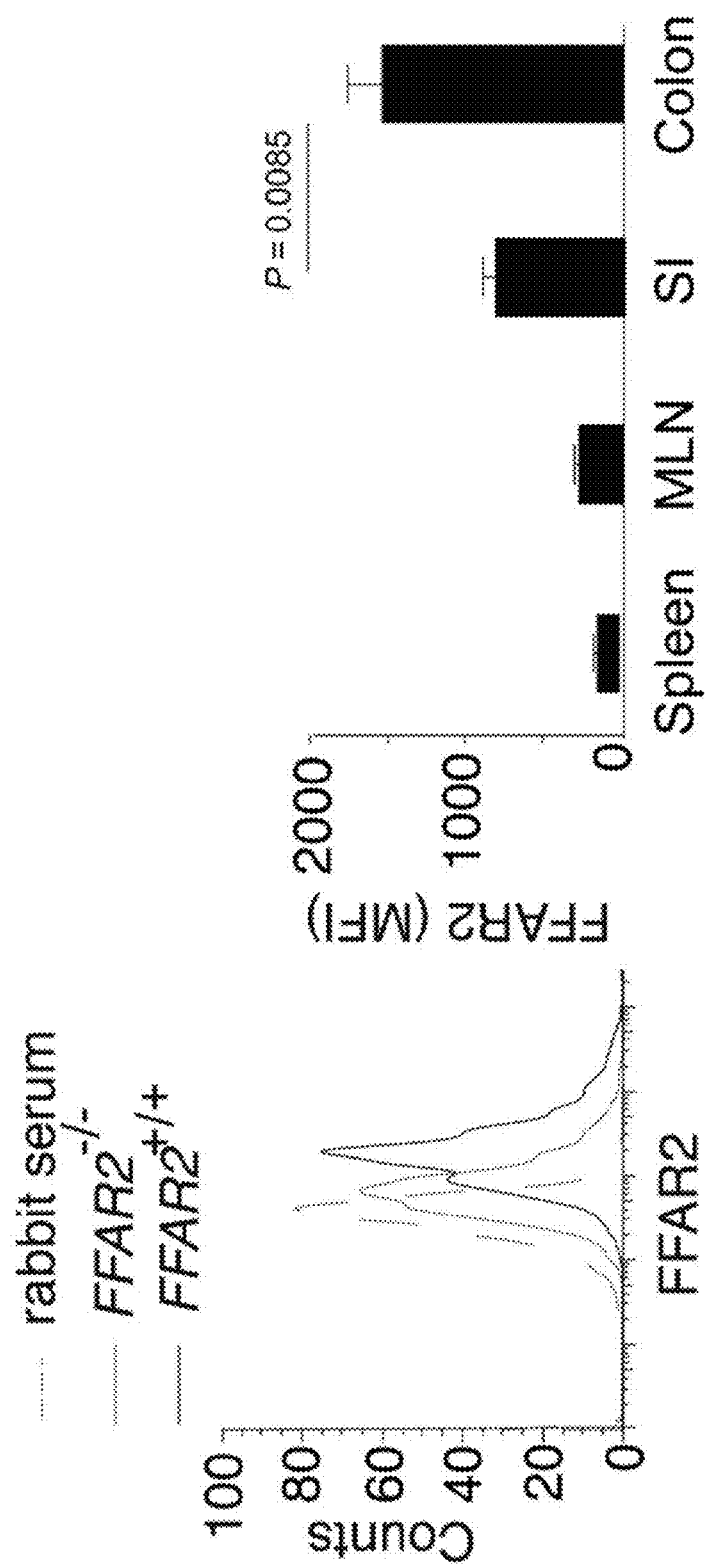
Figure 15C:
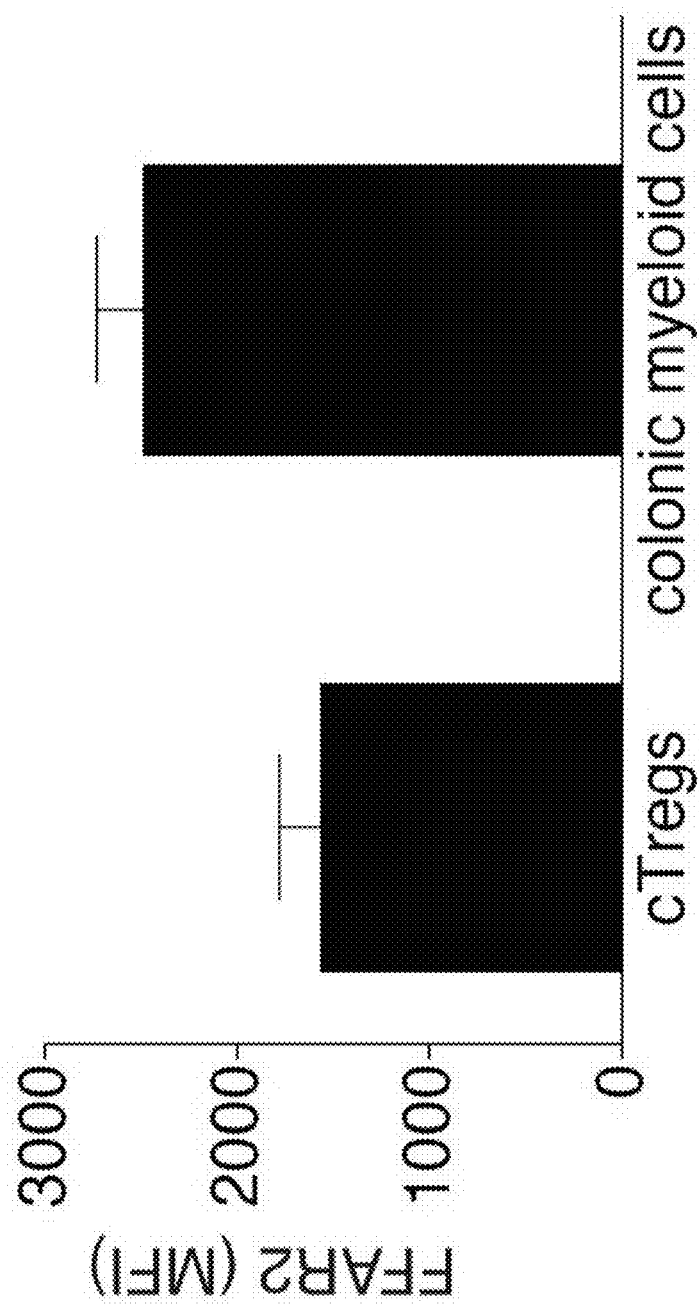

GPR43 expression on $T_{reg}$ isolated from secondary lymphoid tissues (spleen, MLN) was profiled and it was determined that intestinal $T_{reg}$ and, particularly $cT_{reg}$, had significantly higher levels of Ffar2 than $T_{reg}$ isolated from spleen or MLN. As depicted in FIG. 15A and FIG. 15B, on average $cT_{reg}$ had higher levels of Ffar2. This expression seemed dependent upon microbiota-derived signals as intestinal $T_{reg}$ from GF mice had reduced GPR43 expression, on average 4-fold lower for the GF colon (FIG. 15A). As a reference, $cT_{reg}$ Ffar2 expression levels were compared to colonic myeloid (CD11b+) cells, which are known to express Ffar2 and, as shown in FIG. 15C, it was found that on average CD11b+ cells expressed 1.6 fold more Ffar2 than $cT_{reg}$.

Figure 15D:
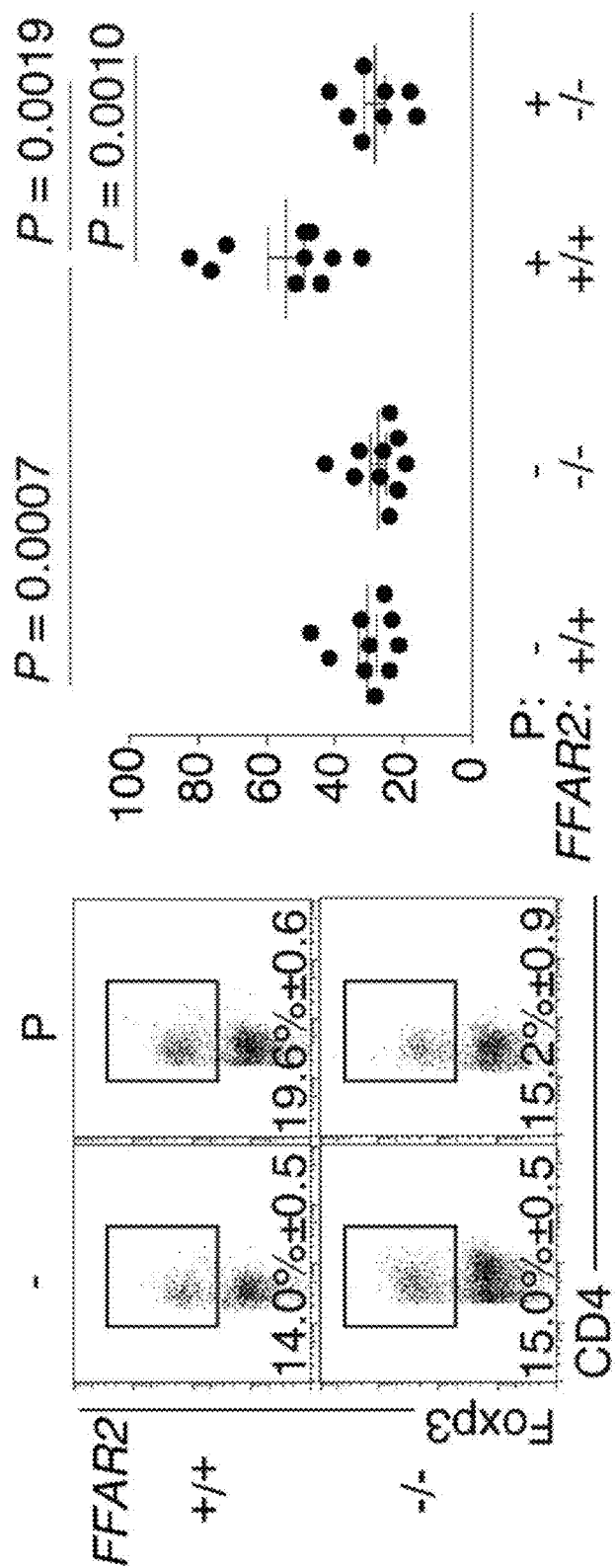
Figure 15E:
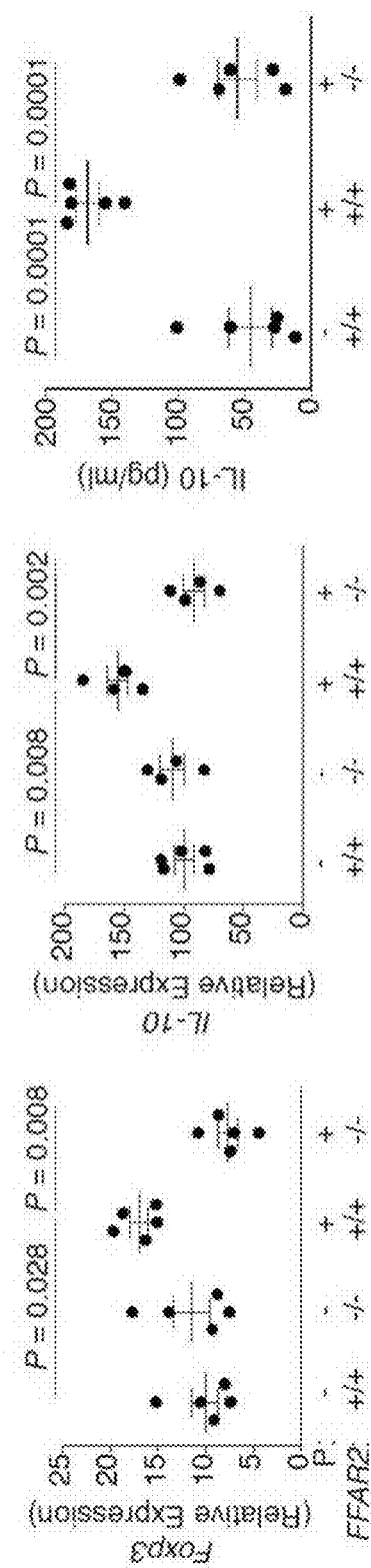
Figure 15F:
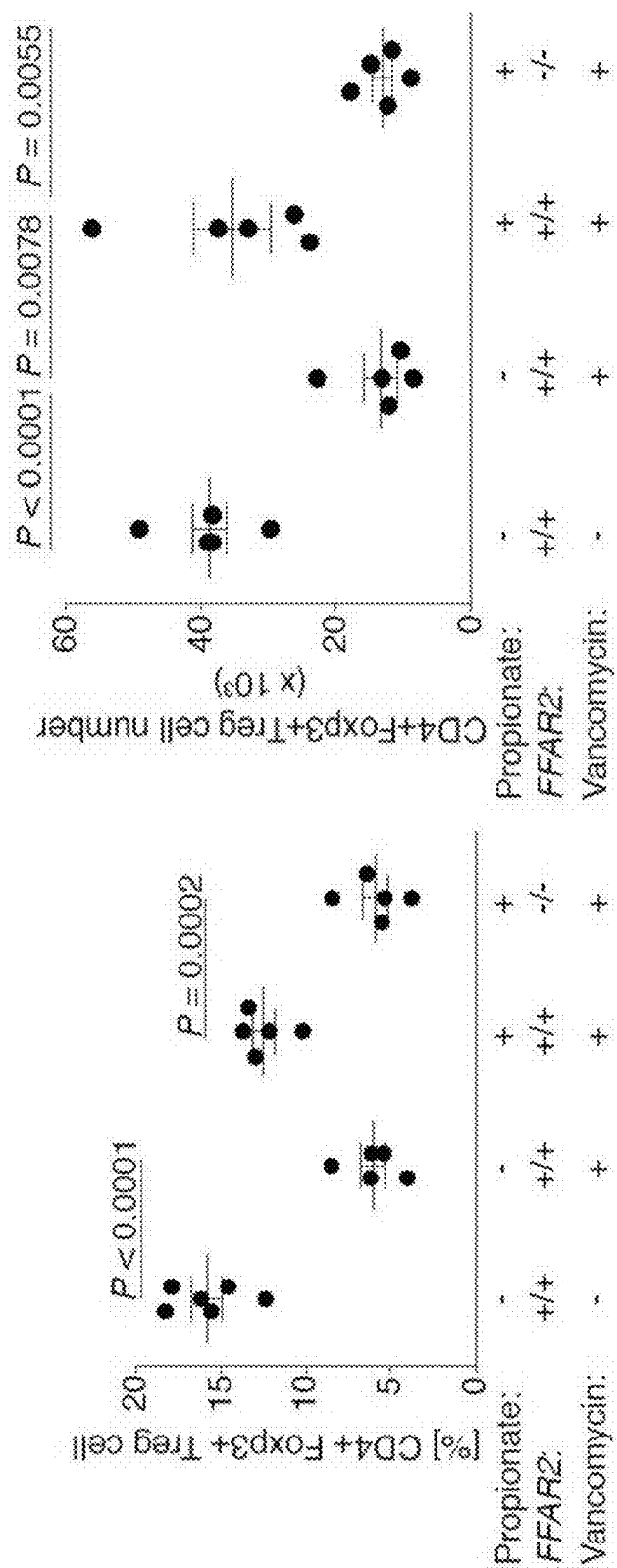
Figure 15G:
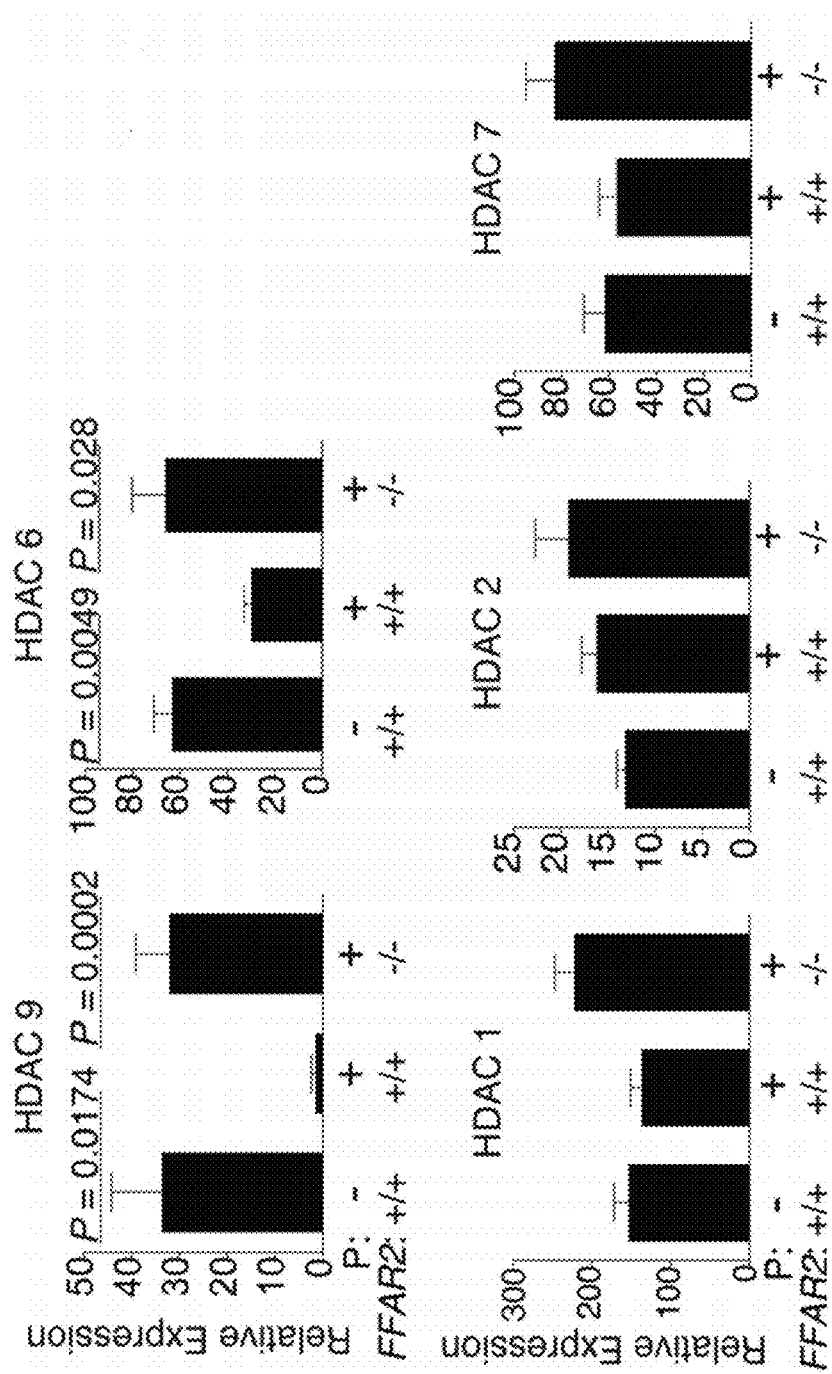
Figure 15H:
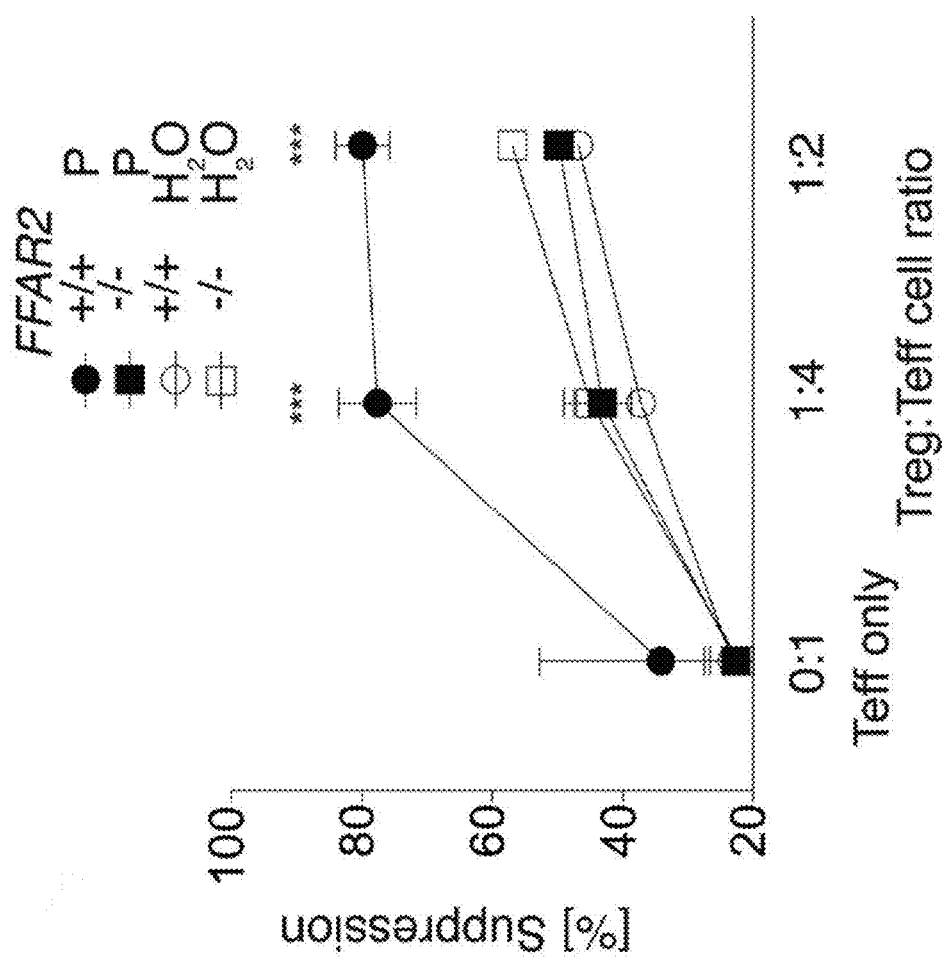

To determine if Ffar2 contributes to $cT_{reg}$ homeostasis and whether GPR43 was responsible for $cT_{reg}$ induction in SPF mice, further investigations were conducted by treating Ffar2−/− mice and Ffar2+/+ littermate control mice with propionate, which has the highest affinity for Ffar2 (Le Poul et al., *J. Biol. Chem.* 278, 25481-25489 (2003)), and $cT_{reg}$ numbers were assessed. As illustrated in FIG. 15D, propionate significantly enhanced the percentage and number of $cT_{reg}$ in Ffar2+/+ control mice but had no effect in Ffar2−/− mice, in which the levels of $cT_{reg}$ were similar to those observed in the water-treated control Ffar2+/+ mice. SCFA-mediated, enhanced $cT_{reg}$ suppressive capacity was also dependent on Ffar2, as shown in FIG. 15H. The foregoing results indicate that Ffar2 is necessary for SCFA-mediated in vivo $cT_{reg}$ induction.

To determine if GPR43 is required for direct stimulation by SCFA, $cT_{reg}$ from Ffar2+/+ and Ffar2−/− mice were isolated and incubated with propionate in vitro. Similar to SPF and GF $cT_{reg}$, propionate enhanced both Foxp3 and IL-10 expression and IL-10 protein levels in Ffar2+/+ $cT_{reg}$, but not in Ffar2−/− $cT_{reg}$, as illustrated in FIG. 15E. Furthermore, the present investigators examined whether propionate could restore $cT_{reg}$ populations and numbers in the setting of vancomycin treatment and, as illustrated in FIG. 15F, Ffar2 was necessary. The foregoing therefore evidences that GPR43 is required for complete induction of $cT_{reg}$ by SCFA.

Figure 15I:
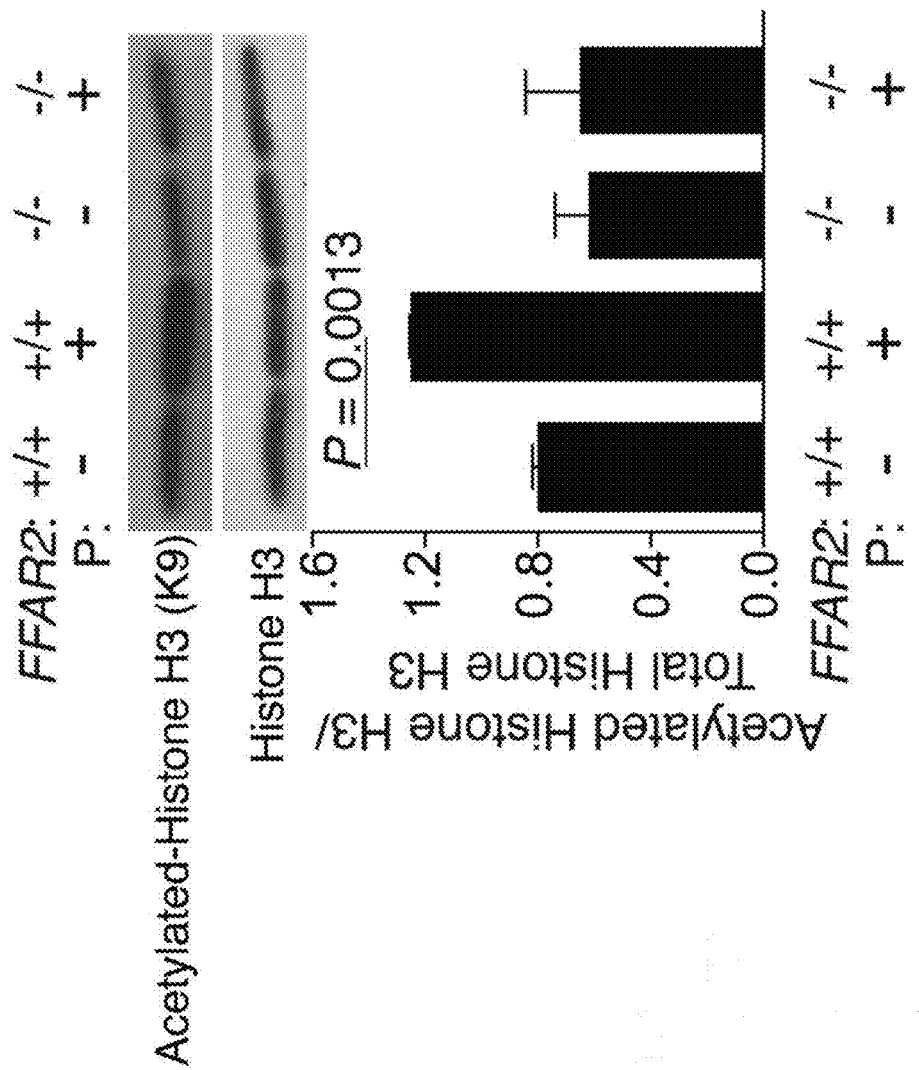

In view of the findings that SCFA can induce $nT_{reg}$, further investigations were conducted to determine whether SCFA mediate their effect through HDAC inhibition. GPR43+/+ and GPR43−/− mice were treated with propionate and HDAC expression was subsequently measured. The HDAC inhibitor trichostatin-A (TSA) increases $T_{reg}$ gene expression and suppressive capacity and HDAC6 and HDAC9 down-regulate $nT_{reg}$ function. Given the findings presented herein that SCFA promote $cT_{reg}$ homeostasis, it was hypothesized that SCFA mediate their effects through HDAC inhibition. As illustrated in FIG. 15G, propionate treatment of Ffar2+/+ mice reduced $cT_{reg}$ expression of HDAC6 and HDAC9 (class IIb and IIa, respectively), but did not reduce expression of the class I HDAC1 and HDAC2 or the class IIa HDAC7. Expression levels in Ffar2−/− were similar to untreated Ffar2+/+ mice. Western blot analysis demonstrated that propionate treatment of $cT_{reg}$ enhanced histone acetylation, which also required the expression of Ffar2, as shown in FIG. 15I.

The foregoing results therefore indicate that SCFA may increase the numbers and suppressive capacity of $cT_{reg}$ through HDAC inhibition through GPR43.

Example 4

Interactions between the gut microbiota and immune cells are critical for intestinal health and dysregulation of these interactions contributes to inflammatory bowel disease (IBD). To test whether SCFA can augment $cT_{reg}$ function in vivo and ameliorate experimental IBD, further investigations were performed utilizing the T cell transfer model of colitis. In this model, lymphopenic mice (e.g., RAG2$^{-/-}$) were injected either with naïve T cells that results in severe colitis, or naïve T cells in combination with T$_{reg}$ which reduces the severity of the colitis.

Figure 16A:
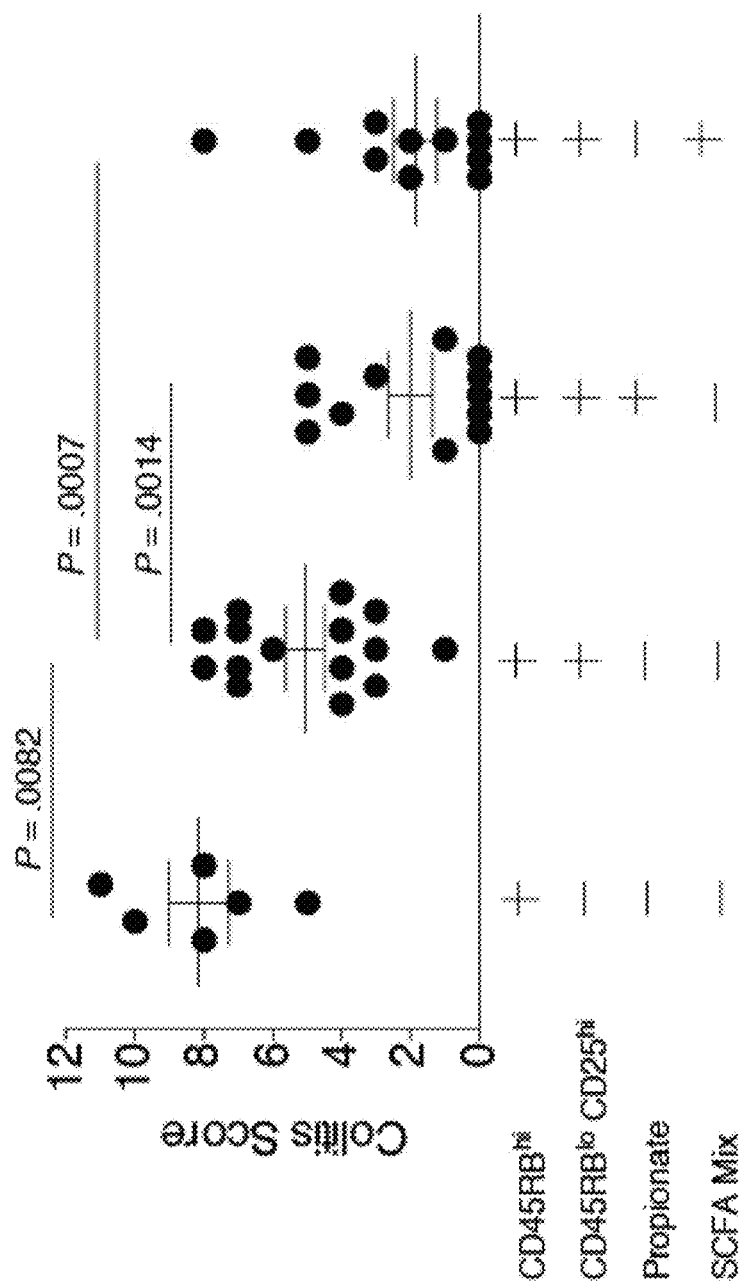
FIGS. 16A and 16B illustrate that SCFA treatment reduced colitis severity and pro-inflammatory cytokine expression and increased IL-10 expression during T cell transfer colitis. BALB/c Rag2$^{-/-}$ mice were injected with CD4$^+$CD45RB$^{hi}$CD25$^-$ naïve T cells alone or in combination with T$_{reg}$. Following injection, mice received propionate, SCFA mix, or pH and sodium-matched drinking water.
Figure 16B:
Figures 17A, 17B, 17C, 17D, 17E, 17F:
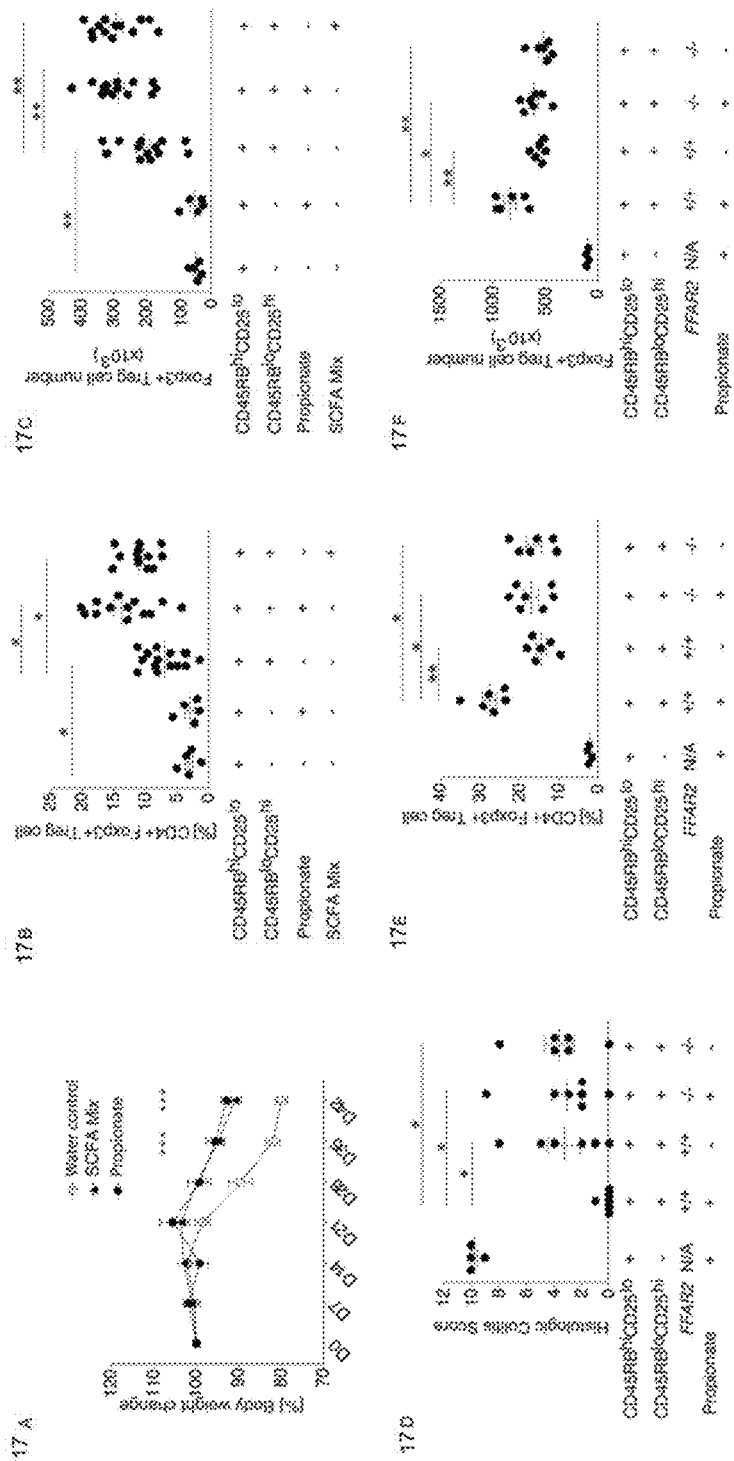
FIGS. 17A-17F illustrate that SCFA exposure ameliorates T cell transfer colitis in a T$_{reg}$-intrinsic, Ffar2-dependent manner. BALB/c Rag2$^{-/-}$ mice were injected with CD4$^+$CD45RB$^{hi}$CD25$^{lo}$ naïve T cells alone or in combination with T$_{reg}$. Following injection, mice received propionate, SCFA mix, or pH and sodium-matched drinking water.

As shown in FIG. 17A, those mice receiving propionate or the SCFA mix with naïve T cells and T$_{reg}$ demonstrated less severe weight loss than those mice that received water alone (P<0.0001). Reduced severity of colitis in the presence of the propionate or the SCFA mix substantiated that these agents augmented the ability of T$_{reg}$ to dampen intestinal inflammation (mean colitis score SCFA mix: 1.9±0.6P=0.0007, propionate: 2.0±0.6P=0.0014 vs. water alone: 5.1±0.6). In contrast, as shown in FIG. 16A those mice receiving only naïve T cells did not have reduced levels of colitis (mean colitis score: 8.2±0.9 vs. T-reg+water alone 5.1±0.6, P=0.03). Representative H&E images are shown for the experimental groups in FIG. 16B, with a 100 µm scale bar shown in the lower left of each image. As shown in FIG. 16B, the propionate and SCFA treated mice demonstrated reduced degrees of colonic crypt injury, inflammation, and hyperplasia compared to control mice.

Figure 18:
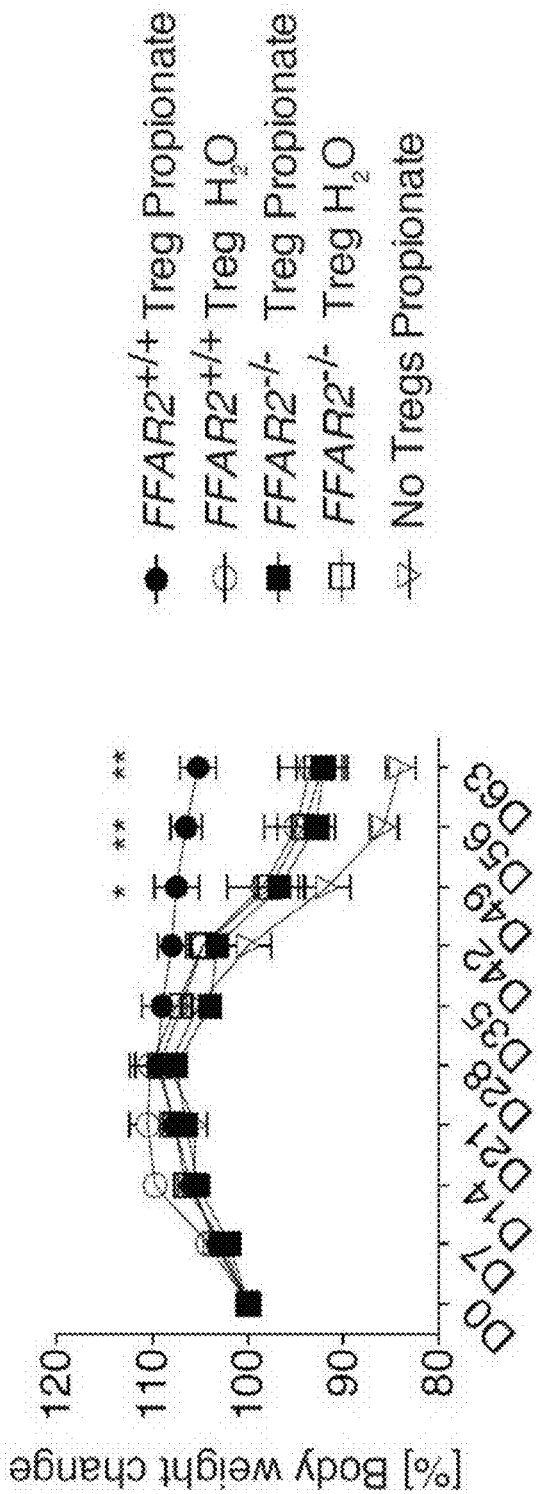
FIG. 18 shows that Ffar2 is required for SCFA-mediated protection against weight loss during T cell mediated colitis. C57BL/6 RAG2$^{-/-}$ mice were injected with CD4$^+$CD45RB$^{hi}$CD25$^+$ naïve T cells alone or in combination with Ffar2$^{+/+}$ or Ffar2$^{-/-}$ T$_{reg}$. Following injection mice received propionate or pH and sodium-matched drinking water. Weekly percentage body weight change is shown across the experimental groups from experimental day 0 through day 63. Each data point is the average of 5-7 individual mice and data are representative of 2 independent experiments. Students' t-test was performed to determine significance, ** indicates P<0.01, * P<0.05. Horizontal lines represent the mean and error bars the SD.
Figure 19:
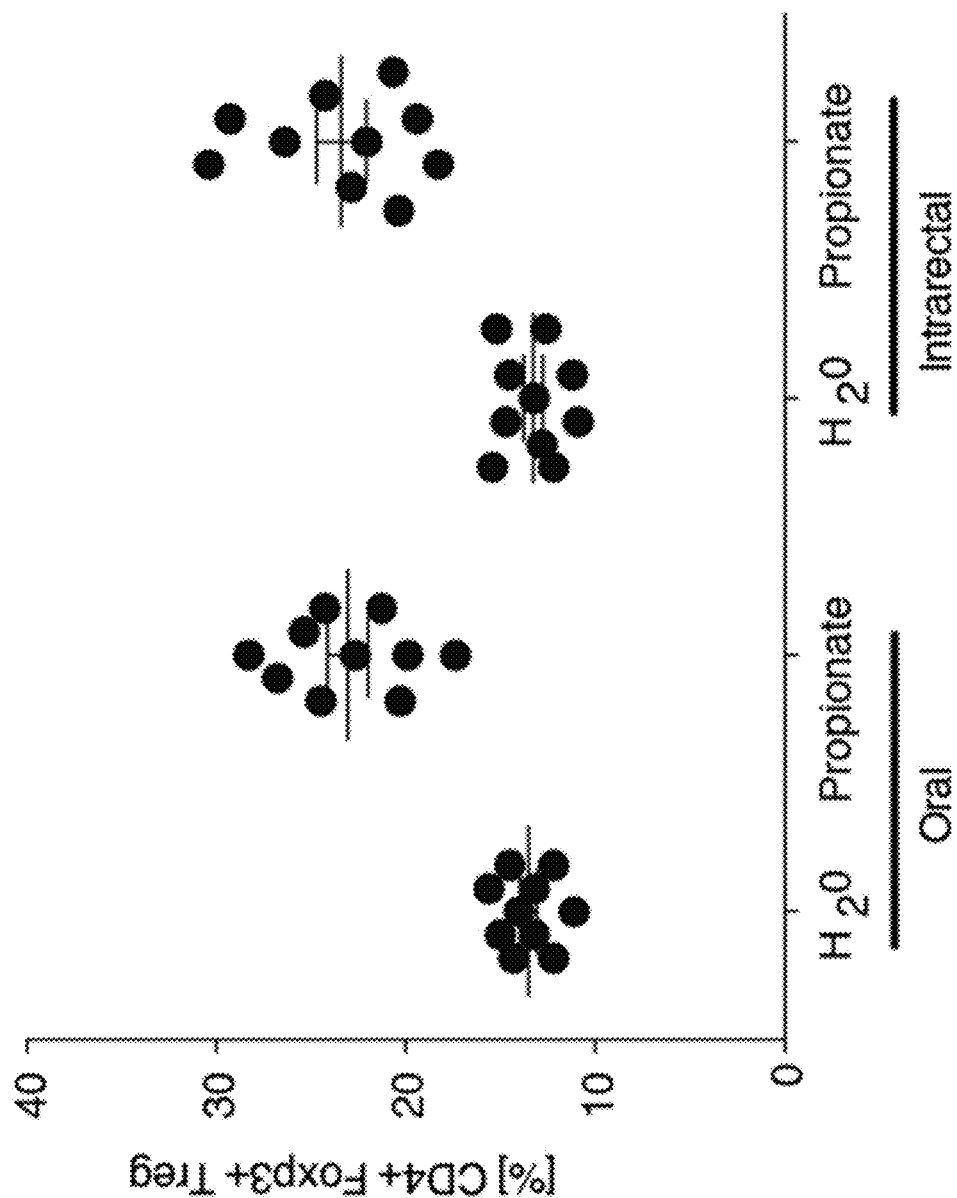
FIG. 19 illustrates that propionate in the drinking water and intrarectal instillation of propionate affect similar changes in colonic T$_{reg}$ populations in SPF mice. Colonic lamina propria (LP) Lymphocytes were isolated and stained for CD45, CD4, and Foxp3 from mice treated with propionate in the drinking water or treated with propionate intrarectally for two weeks. The frequency of CD4$^+$Foxp3$^+$ within the CD45$^+$ population from SPF mice treated with pH- and sodium-matched water alone or propionate is shown. Each symbol represents data from individual mice and show data from two independent experiments. Horizontal lines represent the mean and error bars the SD.

As illustrated in FIGS. 17B and 17C, analysis of the cT$_{reg}$ demonstrated an increase in the frequency and number of colonic LP Foxp3$^+$ T$_{reg}$ in those mice receiving propionate and the SCFA mix. Exposure of the mice to SCFA, however, did not result in conversion of naïve T cells to cT$_{reg}$ (see, FIGS. 17B and 17C, comparing group 1 vs. group 2). To evaluate whether these effects were cT$_{reg}$ intrinsic and dependent upon Ffar2, the present investigators performed the T cell transfer colitis model using RAG2$^{-/-}$ recipients, wild-type naïve T cells and Ffar$^{+/+}$ or Ffar2$^{-/-}$ T$_{reg}$ with or without propionate in the drinking water. As illustrated in FIG. 17D and in FIG. 18, the effect of propionate on intestinal inflammation was dependent upon Ffar2 expression in T$_{reg}$ as indicated by the colitis scores. As shown in FIGS. 17E and 17F, T$_{reg}$ cell populations and cell numbers further substantiated that the propionate effects on cT$_{reg}$ were dependent on Ffar2. The foregoing findings suggest that exposure to SCFA can augment T$_{reg}$ function, which was clinically significant and can ameliorate intestinal inflammation. Additionally, SCFA induced an accumulation of Foxp3$^+$ IL-10$^+$ T$_{reg}$ in the colon of GF and SPF mice, and oral administration of SCFA protected against T cell-driven colitis through enhanced T$_{reg}$ cell function.

The foregoing studies demonstrate that short chain fatty acids (SCFA) are capable of inducing T$_{reg}$ development in germ-free mice and protect against colitis by enhancing T$_{reg}$ population size and function in conventional mice via Ffar2 and GPR43. In the absence of Ffar2, SCFA failed to increase cT$_{reg}$ expression of Foxp3 or the suppressive capacity of cT$_{reg}$. SCFA are potent HDAC inhibitors and treatment of cT$_{reg}$ with SCFAs led to increased histone acetylation and expression of Foxp3 and IL-10, an effect that required Ffar2. The data presented herein reveal a previously unidentified role for Ffar2 and GPR43 linking the adaptive immune system, diet and the gut microbiota to intestinal homeostasis.

The incidence of IBD and other inflammatory diseases (e.g., autoimmune diseases) and obesity is steadily increasing in industrialized nations, and altered interactions between the gut microbiota and host immune system have been invoked as a cause (Lozupone, et al., Nature 489, 220-230 (2012)). The western dietary pattern, specifically reduced ingestion of plant-based fibers, may be a critical factor that links the microbiome and disease (De Filippo et al., Proc. Natl. Acad. Sci. U.S.A. 107, 14691-14696 (2010)). The findings disclosed herein affirm the connectivities between diet, the gut microbiota and immune homeostasis.

Clinically, such results provide evidence that supports the practice of using SCFA to treat patients with colonic inflammation (e.g., IBD, pouchitis, graft versus host disease) and support SCFA and/or dietary interventions that promote SCFA for the treatment of such colonic inflammatory diseases. Collectively, the data presented herein substantiate that SCFA regulate intestinal immune responses, reduce inflammation and can restore intestinal homeostasis and thereby treat colonic inflammation (e.g., inflammatory bowel diseases).

Materials and Methods:

Mice

Figure 20:
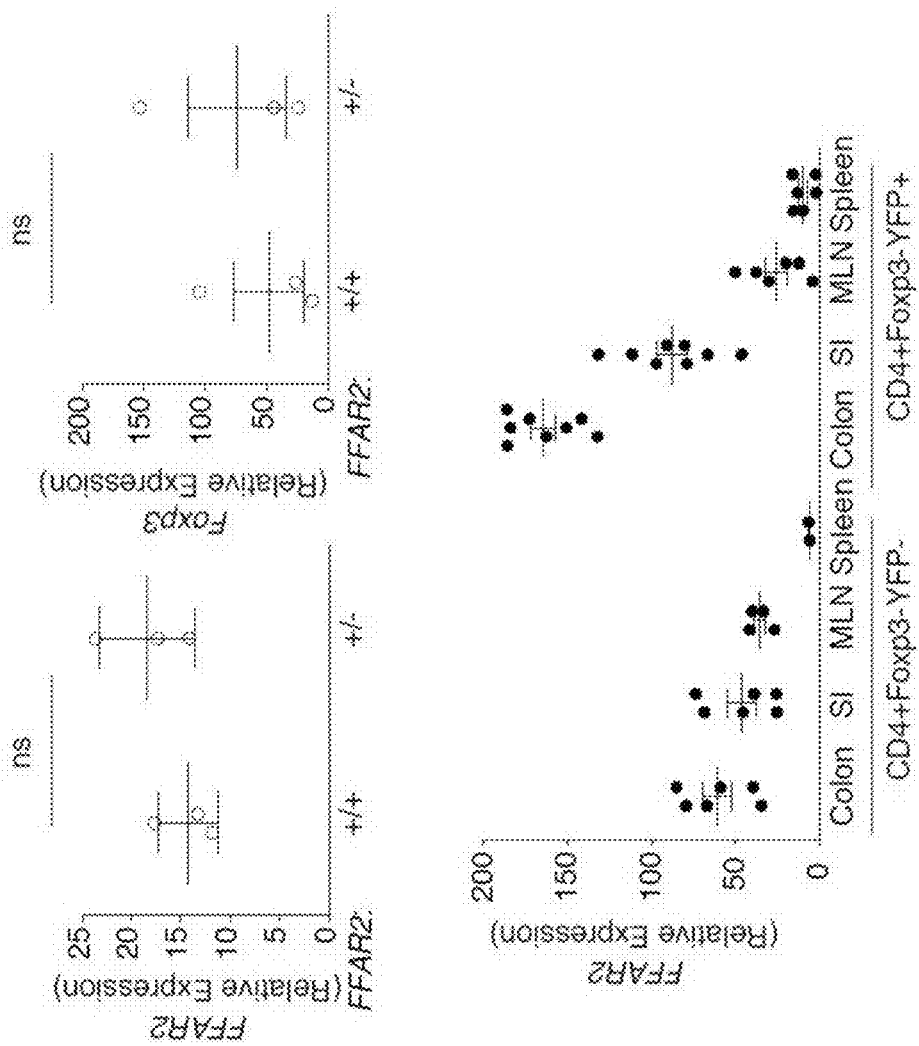
FIG. 20 depicts Ffar2 expression patterns. Upper panels: Colonic lamina propria (LP) lymphocytes were isolated from Ffar2$^{+/-}$ and Ffar2$^{+/+}$ littermates, purified by FACS staining for CD4, CD127, and CD25, and examined ex vivo for expression of Ffar2 and Foxp3 by RTqFCR. Each symbol represents data from 5-8 mice and data reflect three independent experiments. Lower panel: Ffar2 expression levels were examined in Foxp3-YFP$^-$ and Foxp3-YFP$^+$ CD4+ T cells isolated from the colon, small intestine (SI), mesenteric lymph node (MLN), and spleen by RTqPCR. Horizontal lines represent the mean and error bars the SD.

Specified pathogen-free (SPF) mice were bred and housed in microisolator cages in the barrier facility at the Harvard School of Public Health. Mouse studies and experiments were approved and carried out in accordance with Harvard University's Standing Committee on Animals and the National Institutes of Health guidelines for animal use and care. Foxp3$^{YFP-Cre}$ mice on a C57BL/6 background were generously provided by Dr. A. Rudensky (Memorial Sloan Kettering Cancer Center) (Turnbaugh et al., Nature 449, 804-810 (2007)). GPR43−/− mice were produced by Deltagen (Calif., USA) and heterozygous embryos provided by AstraZeneca Transgenic and Comparative Genomic R&D (Molndal, Sweden) (Hooper, et al., Science 336, 1268-1273 (2012)). GPR43 heterozygous cT$_{reg}$ express similar levels of GPR43 and Foxp3 as compared to GPR43 WT cT$_{reg}$ by qPCR. GPR43 expression levels were examined in Foxp3$^-$YFP$^-$ and Foxp3$^-$YFP$^+$ CD4+ T cells isolated from the colon, small intestine, mesenteric lymph node, and spleen by RTqPCR (FIG. 20).

Germ-Free Mouse Experiments

Germ-free (GF) mice were bred and maintained in vinyl positive pressure isolators within the Germ-Free and Gnotobiotic core facilities at the Harvard Digestive Diseases Center at Brigham and Women's Hospital or Children's Hospital Boston. GF experiments were performed at the Brigham and Women's Hospital Germ-Free and Gnotobiotic core facility. Mice were treated for 21 days with either sodium acetate (150 mM), sodium propionate (150 mM), sodium butyrate (100 mM) or a SCFA mix (67.5 mM acetate, 40 mM Butyrate, 25.9 mM Propionate) in the drinking water. In in vivo drinking water treatment experiments, control mice received pH and sodium-matched water. At the conclusion of the experiment mice were removed from isolators and processed immediately. Data on the stability of the SCFA mix solution are provided in Table 1.

SPF SCFA Intervention

For all SPF mouse experiments, mice were treated for 2 weeks with SCFA in the drinking water at the concentrations indicated above and in Smith, et al. Science 341: 1645 (2013). To compare oral versus intra-rectal administration of SCFA, mice were intra-rectally instilled with either 200 µl of propionic acid (50 mM) or pH matched water, for two weeks, using an umbilical vein catheter 3.5 F. For T cell colitis experiments, mice received either sodium propionate (150 mM) or the SCFA mix (described above) in the drinking water beginning at day 0.

Antibiotic Treatment

Mice were treated with vancomycin (500 mg/L; Sigma) in the drinking water for 4 weeks. Fluid intake was monitored and the antibiotic solution was changed every 3 days.

T Cell Transfer Model of Colitis

At Day 0, Naive CD4+ CD25$^-$CD45RB$^{hi}$ splenic T cells were FACS-sorted from BALB/c mice and injected i.p. into 6-8 week old BALB/c RAG2$^{-/-}$ immunodeficient recipients (5×105 cells/mouse). At day 10, BALB/c RAG2$^{-/-}$ immunodeficient recipients received CD4+CD25+CD45RB$^{lo}$ splenic T$_{reg}$ cells (75,000/mouse) isolated from BALB/c or C57BL/6 mice Ffar2$^{+/+}$ and Ffar2$^{-/-}$ mice where indicated. Mice were monitored weekly for weight loss and morbidity for 6-9 weeks as per the protocol's experimental endpoint guidelines.

Lamina Propria (LP) Lymphocyte Isolation

To isolate LP lymphocytes, small and large intestines were collected and opened longitudinally and washed with PBS to remove fecal contents. To remove epithelial cells, mucus and fat tissue, intestines were incubated 2 times in EDTA (5 mM)/DTT (1 mM)/Dulbecco's PBS (calcium and magnesium-free) solution (5 ml/colon) for 25 min at 37° C. Intestines were then minced and collagenase-digested two times for 45 min at 37° C. in RPMI containing 1 mg/ml collagenase type VIII (SIGMA), 25 µg/ml DNase I (Roche), 50 µg/ml Dispase (StemCell Technologies) and 0.01M HEPES (StemCell Technologies). The crude cell suspension was loaded onto a 40%/90% Percoll (GE Healthcare) gradient and centrifuged at 720×g for 25 min at room temperature with acceleration and brake turned off. LP lymphocytes were collected from the 40%/90% interface.

Flow Cytometry Staining

Intracellular staining of the transcription factors Foxp3, Helios and T-bet was performed using the Foxp3 Fix/Perm Buffer Set (Biolegend). For detection of intracellular cytokines, cells were first stimulated for 4 h with 50 ng/ml PMA and 1 µg/ml ionomycin in the presence of Brefeldin A (All obtained from Sigma), followed by staining for surface markers. Cells were then fixed and permeabilized using the Foxp3 Fix/Perm Buffer Set (Biolegend) and stained for intracellular cytokines. The following antibodies were used: PE-labeled anti-Foxp3 (FJK-16s, eBioscience), Pacific Blue-labeled anti-Helios (22F6), PE-, FITC- or APC-labeled anti-CD4 (RM4-5), PECy7-labeled anti-CD3 (145-2C11), PE- or APC-labeled anti-IL-10 (JES5-16E3), PerCP-Cy5.5-labeled anti-IL-17 (TC11-18H10.1), APC- or PE-Cy7-labeled anti-IFNγ (XMG1.2), Pacific Blue-labeled anti-TGFβ1 (TW7-16B4), FITC-, PerCP-Cy5.5 or Pacific Blue-labeled anti-CD45 (30-F11), PerCP-Cy5.5 anti-CD45RB (C363-16A), PE- or FITC-labeled anti-CD25 (PC61), Brilliant Violet 421-labeled anti-CD127 (A7R34), GPR43 rabbit polyclonal (Abcam Catalog #Ab118449, and anti-rabbit IgG DyLight649 (Poly4064). All antibodies were obtained from Biolegend unless otherwise noted. Flow cytometry was performed using LSRII and data were analyzed with FlowJo software (TreeStar, Inc.). Cell sorting was performed using a FACSAriaIlu at the Dana-Farber Cancer Institute Flow Cytometry Core.

SCFA Measurement

Cecal or small intestinal contents were collected immediately after animals were sacrificed and flash frozen in N$_2$(l). Samples were mashed in 500 µl HPLC grade water and centrifuged at >14,000×g, the resulting supernatant was then passed through a 0.22 µm syringe filter to remove bacterial cells and debris. Samples we then acidified with $\frac{1}{10}$ volume of 0.01M H$_2$SO$_4$, heated and passed through a condenser to isolate volatile compounds within a sample. SCFA analyses were performed using an Agilent 1200 series HPLC and a Poroshell 120 SB C18 column (2.7 µm, 3.0×100 mm) with guard column (Agilent Technologies). Sulfuric acid (0.01M) was used as the mobile phase. SCFA concentrations were weight corrected.

Single colonies were inoculated into chopped meat glucose media (Anaerobe Systems) and cultured in an anaerobic hood for 48 hrs at 37° C. Tubes were vortexed, 1 ml of media was transferred to an eppendorf tube, and in parallel serial dilutions were grown on pre-reduced Brucella agar with 5% sheep blood to determine the colony forming units per ml of the liquid cultures. Eppendorf tubes were immediately removed from the anaerobic hood upon collection, spun at 14,000×g for 5 minutes, supernatant was transferred to a fresh tube, and samples were flash frozen until they were processed as described above. A non-inoculated chopped meat glucose media tube was used as a control and processed in the same manner as the experimental samples. No propionate, acetate, or butyrate were detected in the non-inoculated media tube. Butyrate was not detected in any of the culture supernatants and these data are consistent with the short chain fatty profiles published for these species in the Virginia Polytechnic Institute Anaerobe Laboratory Manual Fourth Edition.

RNA Isolation

T$_{reg}$ were isolated from the colon, small intestine, mesenteric lymph node or spleen of C57BL/6 Foxp3$^{YFP-Cre}$ mice and FACS-sorted based on expression of YFP. RNA samples were prepared using the RNeasy Mini Kit (Qiagen) and cDNA was synthesized using the Bio-Rad iScript cDNA Synthesis Kit. Real-time (RT)-qPCR was performed using the KAPA SYBR FAST Universal qPCR Kit (KAPA Biosystems) and a Stratagene MX3005P (Agilent Technologies). The following primer sequences were used:

```
Foxp3:
                                    (SEQ ID NO: 1)
5'-GGCAATAGTTCCTTCCCAGAGTT-3'

(SEQ ID NO: 2)
5'-GGGTCGCATATTGTGGTACTTG-3';

IL-10:
                                    (SEQ ID NO: 3)
5'-TTTGAATTCCCTGGGTGAGAA-3'

(SEQ ID NO: 4)
5'-GGAGAAATCGATGACAGCGC-3';

TGFβ1:
                                    (SEQ ID NO: 5)
5'-CCGCAACAACGCCATCTATG-3'

(SEQ ID NO: 6)
5'-CCCGAATGTCTGACGTATTGAAG-3';

GPR43:
                                    (SEQ ID NO: 7)
5'-AATTTCCTGGTGTGCTTTGG-3'

(SEQ ID NO: 8)
5'-ACCAGACCAACTTCTGGGTG-3';

HDAC1:
                                    (SEQ ID NO: 9)
5'-CCAAGTACCACAGCGATGAC-3'

(SEQ ID NO: 10)
5'-TGGACAGTCCTCACCACG-3';

HDAC2:
                                    (SEQ ID NO: 11)
5'-TGAAGGAGAAGGAGGTCGAA-3'

(SEQ ID NO: 12)
5'-GGATTTATCTTCTTCCTTAACGTCTG-3';

HDAC7:
                                    (SEQ ID NO: 13)
5'-CTCGGCTGAGGACCTAGAGA-3'

(SEQ ID NO: 14)
5'-CAGAGAAATGGAGCCTCTGC-3';
```

```
                                                   -continued
HDAC3:
                                                   (SEQ ID NO: 15)
5'-CACCATGCCAAGAAGTTTGA-3'

(SEQ ID NO: 16)
5'-CCCGAGGGTGGTACTTGAG-3';

HDAC6:
                                                   (SEQ ID NO: 17)
5'-CTGCATGGCATCGCTGGTA-3'

(SEQ ID NO: 18)
5'-GCATCAAAGCCAGTGAGATC-3';

HDAC9:
                                                   (SEQ ID NO: 19)
5'-GCGGTCCAGGTTAAAACAGAA-3'

(SEQ ID NO: 20)
5'-GCCACCTCAAACACTCGCTT-3';

GPR15:
                                                   (SEQ ID NO: 21)
5'-GGAGGACTGGCTCTTTCCTG-3'

(SEQ ID NO: 22)
5'-AAGGCTGGGTGCATGATAGC-3'.
```

In Vitro T Cell Suppression Assay

CD4+CD25− T effector cells ($T_{eff}$) were sorted from spleens of SPF mice and labeled with CFSE (Invitrogen) or Cell Trace Violet (Invitrogen) as per the manufacturer's instructions. $T_{eff}$ cells were plated at $5 \times 10^4$ cells/well in 96-well round-bottom plates with $5 \times 10^4$, CD4 depleted, irradiated (3000 rad) splenocytes, 1 µg/ml anti-CD3 antibody and various numbers of CD4+CD25+ $T_{reg}$ from the colonic lamina propria of SPF mice. Where indicated 0.1 mM sodium acetate, sodium propionate or sodium butyrate was added to the culture. After 96 h, cells were collected and analyzed by flow cytometry.

In Vitro T Cell Stimulation

Colonic lamina propria $T_{reg}$ were isolated from C57BL/6 Foxp3$^{YFP-Cre}$ mice as described above and FACS-sorted based on expression of YFP. Isolated $T_{reg}$ were cultured in RPMI 1640 medium supplemented with 10% FBS (Gibco), 4 mM L-glutamine, 80 U/ml penicillin, 80 µg/ml streptomycin, 1 mM sodium pyruvate, 10 mM HEPES and 1× nonessential amino acids (all obtained from Cellgro). $T_{reg}$ were stimulated with 1 µg/ml anti-CD3 antibody and with or without 0.1 mM sodium propionate for 24 h at 37° C. The division index is calculated by dividing the total number of cell divisions by the number of cells added at the start of the culture and represents the average number of divisions a cell from the original population has undergone and includes the undivided fraction in the calculation.

Western Blot

Colonic lamina propria $T_{reg}$ were isolated and whole cell lysates generated using RIPA buffer in the presence of protease inhibitors. Protein lysates were resolved using SDS-PAGE and transferred to PVDF membrane using a Bio-Rad wet transfer apparatus. Blots were probed with antibodies directed against acetyl-histone H3 (K9) and histone H3 (All from Cell Signaling Technologies). After incubation with the appropriate HRP-conjugated antibody, ECL was used for developing. Densitometry analysis of Western blots was performed using Image-J software available on the world wide web at rsbweb.nih.gov/ij/.

ELISAs

Cytokines were measured in culture supernatants using standard cytokines, antibodies and protocols. IL-10 was measured using the BD OptEIA ELISA Kit (BD Biosciences) and TGFβ1 levels were measured using the mouse TGF-beta 1 DuoSet (R&D Systems).

Histology and Colitis Scores

Colons were excised and cleaned with DPBS prior to fixation in 4% PFA and then processed by routine paraffin embedding, sectioning and H&E staining. Colitis scores were determined by J.N.G., who was blinded to the experimental parameters. Each of 4 histologic parameters were scored as absent (0), mild (1), moderate (2), or severe (3): mononuclear cell infiltration, polymorphonuclear cell infiltration, epithelial hyperplasia, and epithelial injury. The scores for the parameters were summed to generate the cumulative histologic colitis score as previously described.

Statistical Analyses

GRAPHPAD PRISM Software was used for the calculation of statistical measures, including mean values, standard errors, students' t test, Mann-Whitney test and Kruskal-Wallis test.

What is claimed is:

1. A method of increasing the function of colonic regulatory T cells (cT$_{reg}$) in the gastrointestinal tract of a subject, wherein the cT$_{reg}$ express a G-coupled protein receptor 43 (GPR43), and wherein the method comprises contacting the cT$_{reg}$ with an effective amount of a composition comprising one or more short chain fatty acids and thereby increasing the cT$_{reg}$ function.

2. A method of treating colonic inflammation in a subject, wherein the method comprises administering an effective amount of a composition to the subject and thereby treating or preventing colonic inflammation, wherein the composition comprises one or more short chain fatty acids, wherein the composition increases immune function of colonic regulatory T cells (cT$_{reg}$) in the gastrointestinal tract of the subject, and wherein the cT$_{reg}$ express a G-coupled protein receptor 43 (GPR43).

3. A method of reducing the incidence of relapse of inflammatory bowel diseases (IBD) in a subject, wherein the method comprises administering an effective amount of a composition to the subject and thereby reducing the incidence of relapse of IBD, wherein the composition comprises one or more short chain fatty acids, wherein the composition modulates immune response of the subject's colonic regulatory T cells $_{(CTreg)}$, and wherein the cT$_{reg}$ express a G-coupled protein receptor 43 (GRP43).

4. The method of claim 2, wherein the one or more short chain fatty acids interact with the G-coupled protein receptor 43 (GPR43).

5. The method of claim 4, wherein the interaction of the one or more short chain fatty acids with the G-coupled protein receptor 43 (GPR43) inhibits histone deacetylase (HDAC).

6. The method of claim 5, wherein the HDAC is HDAC6.

7. The method of claim 5, wherein the HDAC is HDAC9.

8. The method of claim 2, wherein the one or more short chain fatty acids are selected from the group consisting of formic acid, acetic acid, propionic acid, butyric acid, isobutyric acid, valeric acid, isovaleric acid and pharmaceutically acceptable salts thereof.

* * * * *

SEQUENCE LISTING

```
<160> NUMBER OF SEQ ID NOS: 22

<210> SEQ ID NO 1
<211> LENGTH: 23
<212> TYPE: DNA
<213> ORGANISM: Artificial
<220> FEATURE:
<223> OTHER INFORMATION: primer

<400> SEQUENCE: 1
ggcaatagtt ccttcccaga gtt                                           23

<210> SEQ ID NO 2
<211> LENGTH: 22
<212> TYPE: DNA
<213> ORGANISM: Artificial
<220> FEATURE:
<223> OTHER INFORMATION: primer

<400> SEQUENCE: 2
gggtcgcata ttgtggtact tg                                            22
```

```
<210> SEQ ID NO 3
<211> LENGTH: 21
<212> TYPE: DNA
<213> ORGANISM: Artificial
<220> FEATURE:
<223> OTHER INFORMATION: primer

<400> SEQUENCE: 3
tttgaattcc ctgggtgaga a                                              21

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
ggagaaatcg atgacagcgc                                                20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
ccgcaacaac gccatctatg                                                20

<210> SEQ ID NO 6
<211> LENGTH: 23
<212> TYPE: DNA
<213> ORGANISM: Artificial
<220> FEATURE:
<223> OTHER INFORMATION: primer

<400> SEQUENCE: 6
cccgaatgtc tgacgtattg aag                                            23

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
aatttcctgg tgtgctttgg                                                20

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
accagaccaa cttctgggtg                                                20

<210> SEQ ID NO 9
<211> LENGTH: 20
<212> TYPE: DNA
<213> ORGANISM: Artificial
<220> FEATURE:
<223> OTHER INFORMATION: primer
```

<400> SEQUENCE: 9
ccaagtacca cagcgatgac                                                    20

<210> SEQ ID NO 10
<211> LENGTH: 18
<212> TYPE: DNA
<213> ORGANISM: Artificial
<220> FEATURE:
<223> OTHER INFORMATION: primer

<400> SEQUENCE: 10
tggacagtcc tcaccacg                                                      18

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
tgaaggagaa ggaggtcgaa                                                    20

<210> SEQ ID NO 12
<211> LENGTH: 26
<212> TYPE: DNA
<213> ORGANISM: Artificial
<220> FEATURE:
<223> OTHER INFORMATION: primer

<400> SEQUENCE: 12
ggatttatct tcttccttaa cgtctg                                             26

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
ctcggctgag gacctagaga                                                    20

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
cagagaaatg gagcctctgc                                                    20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
caccatgcca agaagtttga                                                    20

-continued

```
<210> SEQ ID NO 16
<211> LENGTH: 19
<212> TYPE: DNA
<213> ORGANISM: Artificial
<220> FEATURE:
<223> OTHER INFORMATION: primer

<400> SEQUENCE: 16
cccgagggtg gtacttgag                                                19

<210> SEQ ID NO 17
<211> LENGTH: 19
<212> TYPE: DNA
<213> ORGANISM: Artificial
<220> FEATURE:
<223> OTHER INFORMATION: primer

<400> SEQUENCE: 17
ctgcatggca tcgctggta                                                19

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
gcatcaaagc cagtgagatc                                               20

<210> SEQ ID NO 19
<211> LENGTH: 21
<212> TYPE: DNA
<213> ORGANISM: Artificial
<220> FEATURE:
<223> OTHER INFORMATION: primer

<400> SEQUENCE: 19
gcggtccagg ttaaaacaga a                                             21

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
gccacctcaa acactcgctt                                               20

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
ggaggactgg ctctttcctg                                               20

<210> SEQ ID NO 22
<211> LENGTH: 20
<212> TYPE: DNA
<213> ORGANISM: Artificial
<220> FEATURE:
<223> OTHER INFORMATION: primer
```

```
<400> SEQUENCE: 22
aaggctgggt gcatgatagc                                              20
```